US008412309B2

(12) United States Patent
Uchiyama et al.

(10) Patent No.: US 8,412,309 B2
(45) Date of Patent: Apr. 2, 2013

(54) MEDICAL DEVICE GUIDING SYSTEM, MEDICAL DEVICE GUIDING METHOD, AND METHOD FOR CREATING LOOK-UP TABLE TO BE USED IN MEDICAL DEVICE GUIDING SYSTEM

(75) Inventors: Akio Uchiyama, Yokohama (JP); Atsushi Kimura, Akiruno (JP); Johannes Reinschke, Nürnberg (DE); Wolfgang Schmidt, Erlangen (DE)

(73) Assignees: Olympus Medical Systems Corp., Tokyo (JP); Siemens Aktiengesellschaft, Munich (DE)

( * ) Notice: Subject to any disclaimer, the term of this patent is extended or adjusted under 35 U.S.C. 154(b) by 519 days.

(21) Appl. No.: 12/698,444

(22) Filed: Feb. 2, 2010

(65) Prior Publication Data

US 2010/0204566 A1 Aug. 12, 2010

Related U.S. Application Data

(63) Continuation of application No. PCT/JP2008/058728, filed on May 12, 2008.

(30) Foreign Application Priority Data

Aug. 9, 2007 (JP) .................................. 2007-208460

(51) Int. Cl.
*A61B 5/06* (2006.01)
(52) U.S. Cl. ......................... 600/424; 600/407; 600/410
(58) Field of Classification Search .................. 600/407, 600/410, 424
See application file for complete search history.

(56) References Cited

U.S. PATENT DOCUMENTS

| 6,493,573 | B1 | 12/2002 | Martinelli et al. |
| 2006/0169293 | A1* | 8/2006 | Yokoi et al. .................. 128/899 |
| 2007/0185398 | A1 | 8/2007 | Kimura et al. |
| 2008/0306358 | A1 | 12/2008 | Minai |

FOREIGN PATENT DOCUMENTS

| JP | 2006-026391 | 2/2006 |
| JP | 2006-075533 | 3/2006 |
| JP | 2007-000608 | 1/2007 |
| JP | 2007-068967 | 3/2007 |
| WO | WO 2005/112733 A1 | 12/2005 |

OTHER PUBLICATIONS

International Search Report dated Jun. 10, 2008.

\* cited by examiner

*Primary Examiner* — Tse Chen
*Assistant Examiner* — Mark Remaly
(74) *Attorney, Agent, or Firm* — Scully, Scott, Murphy & Presser, P.C.

(57) ABSTRACT

The accurate position detection without being affected by an unnecessary second magnetic field can be realized by calculating the unnecessary second magnetic field induced and generated at positions of magnetic field sensors by a guiding coil arranged the position detection area of the medical device due to an action of a first magnetic field generated by a magnetic field generator, at the time of position detection, and the second magnetic field is subtracted from the first magnetic field detected by the magnetic field sensors to calculate corrected magnetic-field information. Further, LUTs that store beforehand numerical information having a correlation with the second magnetic field induced and generated at the positions of magnetic field sensors are used to calculate the second magnetic field, thereby enabling to reduce an amount of calculation performed each time and realize high speed processing.

58 Claims, 14 Drawing Sheets

MEDICAL DEVICE GUIDING SYSTEM, MEDICAL DEVICE GUIDING METHOD, AND METHOD FOR CREATING LOOK-UP TABLE TO BE USED IN MEDICAL DEVICE GUIDING SYSTEM

CROSS-REFERENCE TO RELATED APPLICATIONS

This application is a continuation-in-part of PCT international application Ser. No. PCT/JP2008/058728 filed on May 12, 2008 which designates the United States, incorporated herein by reference, and which claims the benefit of priority from Japanese Patent Applications No. 2007-208460, filed on Aug. 9, 2007, incorporated herein by reference.

BACKGROUND OF THE INVENTION

1. Field of the Invention

The present invention relates to a medical device guiding system having a position detecting function of detecting a position of a medical device, which is guided to move in a body cavity, a medical device guiding method, and a method for creating a look-up table to be used in the medical device guiding system.

2. Description of the Related Art

Conventionally, as one of medical devices that observe inside a subject, a capsule medical device such as a capsule endoscope has been put to practical use. The capsule endoscope is introduced into a body cavity, and captures images of a desired target region by an image pick-up device incorporated therein at the time of passing through the body cavity. In this case, because an imaging range (angle of view) of the image pick-up device is fixed, a position or direction of the capsule endoscope needs to be guide-controlled so that a desired region to be observed comes within an imaging area. Therefore, as a guiding system therefor, for example, there is a system disclosed in International Publication No. WO05/112733. According to International Publication No. WO05/112733, the position and direction of a capsule endoscope are controlled by causing a guiding magnetic field, by a guiding coil arranged to surround six faces around the capsule endoscope having a built-in magnet, to act on the magnet.

To perform such guiding control as desired, it is essential provide a position detecting device that accurately detects a current position of the capsule endoscope. Therefore, in International Publication No. WO05/112733, an LC resonance circuit including a coil and a capacitor is provided inside the capsule endoscope, the LC resonance circuit is resonated by a magnetic field emitted toward a position detection area of the capsule endoscope, to detect the magnetic field of a specific frequency newly generated due to resonance by a plurality of magnetic field sensors arranged around the position detection area, and the position of the capsule endoscope is acquired from field strength detected by each magnetic field sensor.

Furthermore, as described in U.S. Pat. No. 6,493,573 and Japanese Laid-open Patent Publication No. 2006-75533, the position of the capsule endoscope can be detected also by detecting a magnetic field emitted from outside toward the position detection area of the capsule endoscope by a magnetic field sensor incorporated in the capsule endoscope.

The position detection methods described in International Publication No. WO05/112733, U.S. Pat. No. 6,493,573, and Japanese Laid-open Patent Publication No. 2006-75533 mentioned above use a fact that magnetic field distribution created in space by a coil can be calculated in theory. Therefore, it is not desirable that a conductor or a magnetic body that will possibly disturb the magnetic field distribution exists in the position detection area.

Therefore, U.S. Pat. No. 6,493,573 discloses a method for correcting data by acquiring a time constant of an eddy current by a magnetic field of a different frequency, because position detection accuracy decreases if the eddy current flows into an interfering body existent in a position detection area. Furthermore, there is also disclosed a method in which magnetic field distribution generated by calculating and taking into consideration an effect by an interfering body (a shield member) is held in a look-up table (LUT) and read.

SUMMARY OF THE INVENTION

A medical device guiding system according to an aspect of the present invention includes a medical device having a built-in magnet and introduced into a body cavity; a position detecting device having a magnetic field generator and a magnetic field detector, with a part thereof being incorporated in the medical device, in which the magnetic field generator generates a first magnetic field of a specific frequency and the magnetic field detector detects detected magnetic-field information including the first magnetic field of the specific frequency, to detect at least one of a position and an orientation of the medical device; and a magnetic guiding device having a guiding coil that generates a guiding magnetic field for changing at least one of the position and the orientation of the medical device by acting on the magnet, and a drive unit connected to the guiding coil to supply power for generating the guiding magnetic field. The position detecting device includes a specific position detection area for estimating at least one of the position and the orientation of the medical device. The position detecting device includes a look-up table that stores a plurality of pieces of numerical information having a correlation with a second magnetic field induced at a position of the magnetic field detector by at least one of the guiding coil and the magnetic field generator due to the action of the first magnetic field, when the medical device is arranged at a plurality of specific positions in a plurality of specific orientations; a magnetic field calculator that estimates the second magnetic field by referring to the look-up table based on the position and the orientation of the medical device; a magnetic-field extracting unit that calculates corrected magnetic-field information obtained by subtracting the second magnetic field estimated by the magnetic field calculator from the first magnetic field detected by the magnetic field detector; and a position calculator that estimates the position and the orientation of the medical device based on the corrected magnetic-field information calculated by the magnetic-field extracting unit.

A medical device guiding method according to another aspect of the present invention is for guiding and controlling a position or an orientation of a medical device having a built-in magnet and introduced into a body cavity, based on a result of detecting the position and the orientation of the medical device from a first magnetic field of a specific frequency, by using a position detecting device having a magnetic field generator and a magnetic field detector, with a part thereof being incorporated in the medical device. The method includes generating a guiding magnetic field acting on the magnet by a guiding coil supplied with power from a drive unit to control the position or the orientation of the medical device; generating a first magnetic field of a specific frequency by the magnetic field generator; detecting a magnetic field including the first magnetic field generated at the magnetic-field generating step by the magnetic field detector;

estimating, by referring to a look-up table based on the position and the orientation of the medical device, a second magnetic field that is induced, at a position of the magnetic field detector, due to the action of the first magnetic field by at least one of the guiding coil and the magnetic field generator, when the medical device is arranged at a plurality of specific positions in a plurality of specific orientations, the look-up table storing a plurality of pieces of numerical information having a correlation with the second magnetic field; calculating corrected magnetic-field information obtained by subtracting the estimated second magnetic field from the detected magnetic field; and estimating the position and the orientation of the medical device based on the calculated corrected magnetic-field information.

A method according to still another aspect of the present invention is for creating a look-up table to be used in a medical device guiding system. The system includes a medical device having a built-in magnet and introduced into a body cavity; a position detecting device incorporated in the medical device and having a magnetic field generator including an emission coil and an oscillation circuit to generate a first magnetic field of a specific frequency, and a magnetic field detector including a plurality of magnetic field sensors arranged around a position detection area of the medical device to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field. The method includes setting a plurality of discrete specific positions and a plurality of discrete specific orientations within the position detection area; calculating a magnetic flux penetrating a plurality of guiding coils arranged at known positions around the position detection area when the medical device is arranged at one specific position and in one specific orientation to generate the first magnetic field; calculating an induction current flowing in the guiding coils based on calculated magnetic flux; calculating numerical information having a correlation with a second magnetic field induced at the magnetic field sensors, when the calculated induction current flows in the guiding coils; storing the calculated numerical information having the correlation with the second magnetic field in association with the one specific position and the one specific orientation; and creating a table by repeating the calculating the magnetic flux, the calculating the induction current, the calculating the numerical information, and the storing for all the specific positions and the specific orientations, by sequentially changing the one specific position and the one specific orientation.

A method according to still another aspect of the present invention is for creating a look-up table to be used in a medical device guiding system. The system includes a medical device having a built-in magnet and introduced into a body cavity; a position detecting device incorporated in the medical device and having a magnetic field generator including an emission coil and an oscillation circuit to generate a first magnetic field of a specific frequency and a magnetic field detector including a plurality of magnetic field sensors arranged around a position detection area of the medical device to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field. The method includes setting a plurality of discrete specific positions and a plurality of discrete specific orientations within the position detection area; calculating mutual inductance with a plurality of guiding coils arranged at known positions around the position detection area when the medical device is arranged at one specific position and in one specific orientation to generate the first magnetic field; calculating an induction current flowing in the respective guiding coils based on calculated mutual inductance; calculating numerical information having a correlation with a second magnetic field induced at the magnetic field sensors arranged around the position detection area to detect the first magnetic field, when the calculated induction current flows in the guiding coils; storing the calculated numerical information having the correlation with the second magnetic field in association with the one specific position and the one specific orientation; and creating a table by repeating the calculating the induction current, the calculating the numerical information, and the storing for all the specific positions and specific orientations, by sequentially changing the one specific position and the one specific orientation.

A method according to still another aspect of present invention is for creating a look-up table to be used in a medical device guiding system. The system includes a medical device having a built-in magnet and introduced into a body cavity; a position detecting device that includes a magnetic field generator including a drive coil arranged around a position detection area of the medical device to generate a magnetic field for position detection and a resonance circuit including an emission coil and a capacitor, incorporated in the medical device to resonate due to the magnetic field for position detection, thereby generating a first magnetic field of a specific frequency, and a magnetic field detector including a plurality of magnetic field sensors arranged around the position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field. The method includes setting a plurality of discrete specific positions and a plurality of discrete specific orientations within the position detection area; calculating a magnetic flux penetrating a plurality of guiding coils arranged at known positions around the position detection area or the drive coil, when the medical device is arranged at one specific position and in one specific orientation to generate the first magnetic field; calculating an induction current flowing in the guiding coils or the drive coil based on the calculated magnetic flux; calculating numerical information having a correlation with a second magnetic field induced at positions of the magnetic field sensors, when the calculated induction current flows in the guiding coils or the drive coil; storing the calculated numerical information having the correlation with the second magnetic field in association with the one specific position and the one specific orientation; and creating a table by repeating the calculating the magnetic flux, the calculating the induction current, the calculating the numerical information, and the storing for all the specific positions and the specific orientations, by sequentially changing the one specific position and the one specific orientation.

A method according to still another aspect of the present invention is for creating a look-up table to be used in a medical device guiding system. The system includes a medical device having a built-in magnet and introduced into a body cavity; a position detecting device that includes a magnetic field generator including a drive coil arranged around a position detection area of the medical device to generate a magnetic field for position detection and a resonance circuit including an emission coil and a capacitor, incorporated in the medical device to resonate due to the magnetic field for position detection, thereby generating a first magnetic field of a specific frequency, and a magnetic field detector including a plurality of magnetic field sensors arranged around the position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field. The method includes setting a plurality of discrete specific positions and a plurality of discrete specific orientations within the position detection area; calculating mutual inductance with a plurality of guiding coils arranged at known positions around the position detection area or the drive coil, when the medical device is arranged at one specific position and in one specific orientation to generate the first magnetic field; calculating an induction current flowing in the respective guiding coils or the drive coil based on the calculated mutual inductance; calculating numerical information having a correlation with a second magnetic field induced at positions of the magnetic field sensors arranged around the position detection area to detect the first magnetic field, when the calculated induction current flows in the guiding coils or the drive coil; storing the calculated numerical information having the correlation with the second magnetic field in association with the one specific position and the one specific orientation; and creating a table by repeating the calculating the induction current, the calculating the numerical information, and the storing for all the specific positions and the specific orientations, by sequentially changing the one specific position and the one specific orientation.

A method according to still another aspect of the present invention is for creating a look-up table to be used in a medical device guiding system. The system includes a medical device having a built-in magnet and introduced into a body cavity; a position detecting device having a magnetic field generator including a plurality of emission coils arranged around a position detection area of the medical device to generate a first magnetic field of a specific frequency and a magnetic field detector including a magnetic field sensor incorporated in the medical device to detect the first magnetic field, thereby detecting a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field. The method includes setting a plurality of discrete specific positions and a plurality of discrete specific orientations within the position detection area; calculating an induction current flowing in the guiding coil or the emission coil arranged at a known position around the position detection area, when the medical device is arranged at one specific position and in one specific orientation to generate the first magnetic field of a specific frequency with respect to the position detection area by the emission coil; calculating numerical information having a correlation with a second magnetic field induced at a position of the magnetic field sensor, when the calculated induction current flows in the guiding coil or the emission coil; storing the calculated numerical information having the correlation with the second magnetic field in association with the one specific position and the one specific orientation; and creating a table by repeating the calculating the induction current, the calculating the numerical information, and the storing for all the specific positions and specific orientations, by sequentially changing the one specific position and the one specific orientation.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a medical device guiding system, a medical device guiding method, and a method for creating a look-up table to be used in the medical device guiding system according to the present invention will be explained below in detail with reference to the accompanying drawings. The present invention is not limited to the embodiments.

First Embodiment

Figure 1:
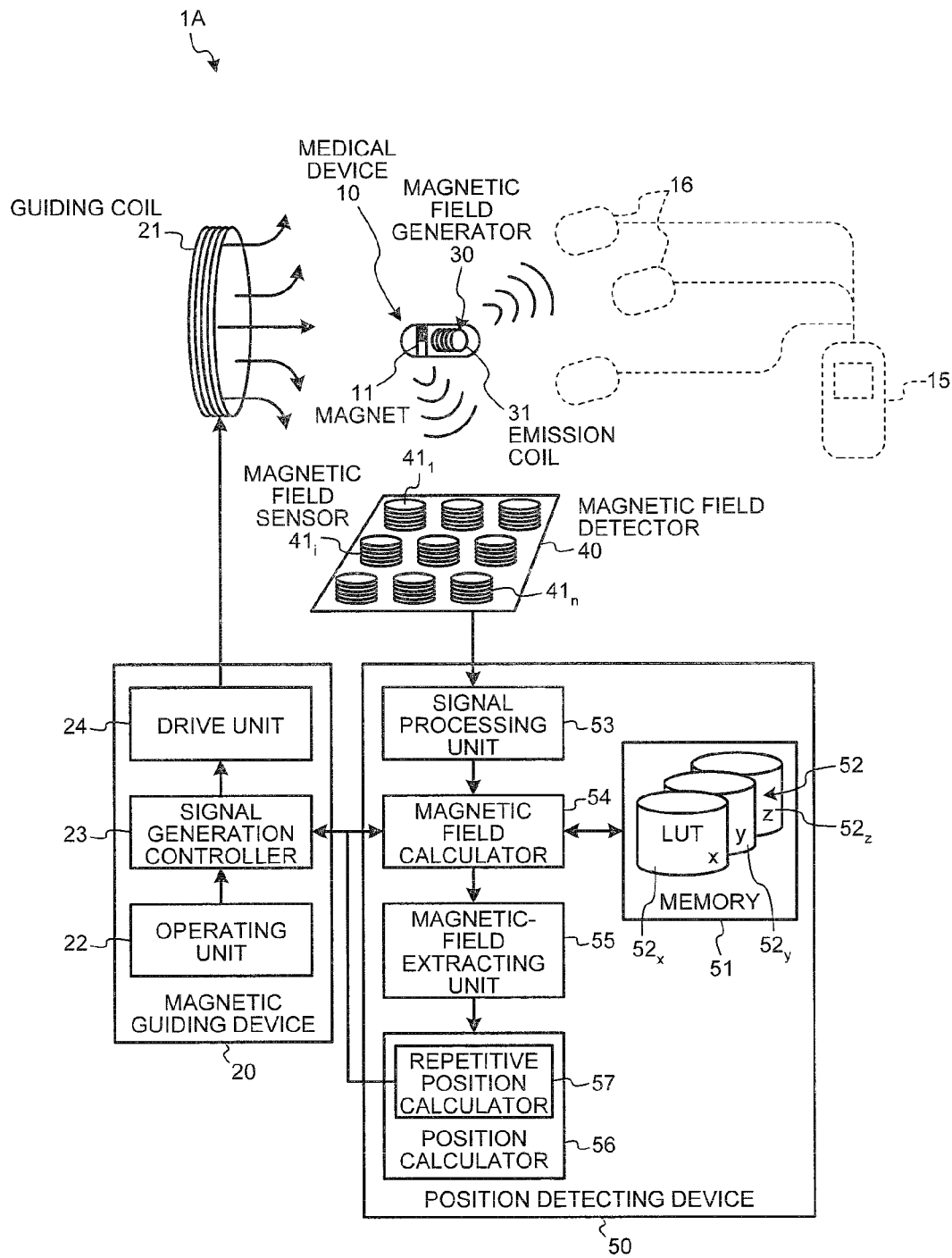
FIG. 1 is a schematic diagram of a fundamental configuration example of a medical device guiding system according to a first embodiment of the present invention.

FIG. 1 is a schematic diagram of a fundamental configuration example of a medical device guiding system according to a first embodiment of the present invention. A medical device guiding system 1A according to the first embodiment generally includes a capsule medical device 10, a magnetic guiding device 20, and a position detecting device 50.

The medical device 10 is a capsule endoscope including, for example, a cylindrical capsule container sealed by a watertight structure and introduced into a body cavity of a subject. The medical device 10 includes an imaging unit (not shown) that captures an image inside the body cavity, a signal processing unit (not shown) that processes a captured signal, a wireless transmitter (not shown) that wirelessly transmits the processed signal to the outside of the subject or the like, and has an imaging function and a wireless communication function. The medical device guiding system includes an external receiving device 15 arranged outside the subject corresponding to the medical device 10. The external receiving device 15 has a plurality of antennas 16 arranged at a plurality of places on a body surface of the subject to receive a signal wirelessly output from the medical device 10, to wirelessly receive and accumulate signals associated with the captured images via the antennas 16.

The medical device 10 includes a magnet 11 such as a permanent magnet fixed and arranged at a position having no problem in capturing inside images to generate a driving force for changing a position or direction by receiving an action of a guiding magnetic field.

The magnetic guiding device 20 changes the position or direction of the medical device 10 by causing the guiding magnetic field to act on the magnet 11 in the medical device 10 introduced into the body cavity from outside of the subject, and includes a guiding coil 21, an operating unit 22, a signal generation controller 23, and a drive unit 24. As the position detecting device 50 is arranged at a predetermined position around the subject in a position detection area for detecting the position of the medical device 10, and the guiding coil 21 emits the guiding magnetic field to the magnet 11 in the medical device 10 introduced into the subject.

The operating unit 22 includes an input device such as a joystick to instruct a moving direction or orientation of the medical device 10 intended by an operator, or a keyboard, a panel switch or the like to perform information input and various settings. The signal generation controller 23 calculates a signal waveform required for guiding the medical device 10 based on an instruction from the operating unit 22 and the position information from the position detecting device 50 described later, to generate a waveform based on a calculated result by controlling the drive unit 24. The drive unit 24 causes a drive current to flow in the guiding coil 21 to generate a guiding magnetic field. Strength of the guiding magnetic field generated for moving the medical device 10 is relatively large, and an output impedance of the drive unit 24 is set small to reduce a loss.

The position detecting device 50 generally includes a magnetic field generator 30 and a magnetic field detector 40. The magnetic field generator 30, which is a part of the position detecting device 50, is incorporated in the medical device 10, and the magnetic field detector 40 is arranged around the position detection area to detect a first magnetic field of a specific frequency generated by the magnetic field generator 30, thereby detecting the position and orientation of the medical device 10.

The magnetic field generator 30 generates the first magnetic field of a specific frequency with respect to the position detection area of the medical device 10 including an XYZ coordinate system in which an origin position is set. The magnetic field generator 30 includes an emission coil 31 incorporated in the medical device 10 and an oscillation circuit (not shown). That is, the magnetic field generator 30 according to the first embodiment is formed as a self-excited magnetic field generator that generates an induction field in the emission coil 31 by the oscillation circuit to generate the first magnetic field of the specific frequency toward outside. The specific frequency of the generated first magnetic field is set as an angular frequency ω[rad].

The magnetic field detector 40 detects the first magnetic field of the specific frequency generated with respect to the position detection area by the magnetic field generator 30. The magnetic field detector 40 includes a plurality of magnetic field sensors 41a to 41n arranged around the position detection area with respect to the emission coils 31 paired and incorporated in the medical device 10. These magnetic field sensors 41a to 41n convert an alternating magnetic field of the specific frequency that pass through the respective coils into voltage for detection.

The position detecting device 50 according to the first embodiment also includes a look-up table (LUT) 52 held by a memory 51, a signal processing unit 53, a magnetic field calculator 54, a magnetic-field extracting unit 55, and a position calculator 56.

The LUT 52, which is described later in detail, stores numerical information having a correlation with an unnecessary second magnetic field of a specific frequency induced at a position of the magnetic field detector 40 (the magnetic field sensors 41a to 41n) by the guiding coil 21 due to the action of the first magnetic field, designating a plurality of specific positions and a plurality of specific orientations of the medical device 10 as variables, when the medical device 10 is arranged at the specific positions and the specific orientations preset in the position detection area. The signal processing unit 53 converts a voltage signal acquired from the magnetic field detector 40 into digital data required for position calculation, and evaluates the magnetic field detected by the magnetic field detector 40 and the digital signal to acquire current position information and current orientation information of the medical device 10 estimated from position distribution data.

The magnetic field calculator 54 estimates the second magnetic field by referring to the look-up table 52, assuming the current position and the current orientation of the medical device 10 sequentially estimated in optimization calculation in the position calculator 56 as the specific position and the specific orientation. The magnetic-field extracting unit 55 calculates corrected magnetic-field information acquired by subtracting the second magnetic field estimated by the magnetic field calculator 54 from the first magnetic field detected by the magnetic field detector 40. The position calculator 56 includes a repetitive position calculator 57 that repetitively performs optimization calculation until the corrected magnetic-field information calculated by the magnetic-field extracting unit 55 substantially matches the magnetic field (theoretical value) calculated from the position and orientation of the medical device 10, to estimate the position and orientation of the medical device 10.

A basic position detecting operation performed by the position detecting device 50 when it does not include the LUT 52 and the magnetic field calculator 54 is explained here. It is assumed here that nine magnetic field sensors $41_1$ to $41_n$ (n=9) are discretely arranged in a 3×3 matrix in the magnetic field detector 40. That is, when the emission coil 31 in the medical device 10 is only one, as an example of position calculation explained here, $$\vec{M} = [M_x, M_y, M_z]$$

at least six magnetic field sensors 41 are required for obtaining six variables in total of a position coordinate [x, y, z] in the XYZ coordinate system of the medical device 10 and a magnetic dipole moment.

Under such a circumstance, output signals $V_{d1}, V_{d2}, \ldots, V_{dn}$ from the respective magnetic field sensors $41_1$ to $41_n$ of the magnetic field detector 40 are output to the magnetic-field extracting unit 55 through signal processing by the signal processing unit 53. The magnetic-field extracting unit 55 obtains magnetic field strengths $B_{d1}, B_{d2}, \ldots, B_{dn}$ passing through the respective magnetic field sensors $41_1$ to $41_n$ by applying a simple proportionality coefficient to respective pieces of voltage information.

It is expressed that the medical device 10 is in a certain orientation at a certain coordinate position in the position detection area with one orientation as P vector as described below, $$\vec{p} = (x, y, z, M_x, M_y, M_z)$$

and a position of the ith magnetic field sensor $41_i$ is assumed as:

$$\vec{r}_{si} = [x_i, y_i, z_i]$$

When a distance vector between P vector and the ith magnetic field sensor $41_i$ is obtained as described below:

$$\vec{r}_i = [x_i - x, y_i - y, z_i - z]$$

the magnetic field generated by the magnetic dipole moment is $$\vec{B}_i = \frac{1}{4\pi} \left\{ \frac{3(\vec{M} \cdot \vec{r}_i)}{r_i^5} \vec{r}_i - \frac{\vec{M}}{r_i^3} \right\}$$

expressed as above.

The position detecting device 50 normally uses an actual measurement value $B_{di}$ and a theoretical value (estimated value) $B_i$ to create an evaluation function as described below:

$$\sum_{i=1}^{n} \left( \vec{B}_{di} - \vec{B}_i(\vec{p}) \right)^2 = 0$$

and performs optimization calculation such as a least-square method, thereby enabling to obtain P vector representing the position coordinate and the orientation of the medical device 10.

Figure 2:
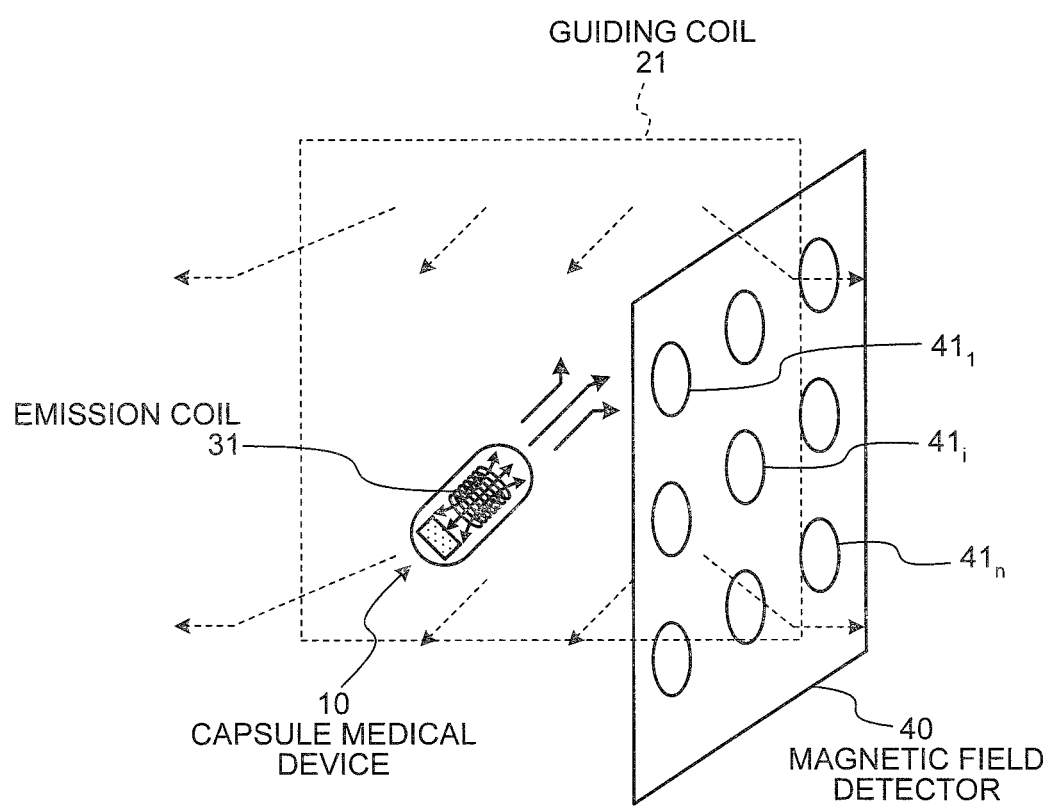
FIG. 2 is an explanatory diagram of a state that an unnecessary magnetic field is generated.

In practice, however, when the guiding coil 21 for magnetic guidance is arranged around the position detection area, as shown in FIG. 2, the guiding coil 21 induces and generates the unnecessary second magnetic field at the position of the magnetic field sensors $41_1$ to $41_n$ upon reception of the action of the first magnetic field of the specific frequency generated by the emission coil 31. In FIG. 2, the dotted-line square represents the guiding coil 21, and the solid-line square represents the magnetic field detector 40 having the magnetic field sensors $41_1$ to $41_n$. That is, the first magnetic field generated from the emission coil 31 incorporated in the medical device 10 passes through not only the magnetic field detector 40 but also the guiding coil 21. Therefore, if an induced current actually flows in the guiding coil 21 due to some load connected to the guiding coil 21, the second magnetic field, as shown by a broken-line arrow, negating the passed magnetic field is induced and generated. Because a part of the second magnetic field passes through the position of the magnetic field sensors $41_1$ to $41_n$ of the magnetic field detector 40, a detection output of the magnetic field sensors $41_1$ to $41_n$ includes components other than the first magnetic field component, thereby adversely affecting position detection.

The unnecessary second magnetic field can be calculated by calculation described below. An opening of the rectangular guiding coil 21 is divided by a constant small area $\Delta S$ to divide the opening into T (for example, T=20×20=400), and a center thereof is set as a point of interest as the position of each small area $\Delta S$. If it is assumed that the position of the medical device 10 having the built-in emission coil 31 and the presence of the magnetic dipole moment are expressed by P vector, the magnetic field strength at the respective points of interest can be calculated. This calculation is performed with respect to an inner surface of the guiding coil 21, and all values are added up and multiplied by the small area $\Delta S$, thereby obtaining a magnetic flux $\Phi_g$ passing through the guiding coil 21 as a function of P vector.

$$\Phi_g(\vec{P}) = \sum \Delta S \cdot \vec{B}_g(\vec{P}) = \Delta S \cdot \sum_{k=1}^{T} \vec{B}_{gk}(\vec{P})$$

When it is assumed that the number of turns of the guiding coil 21 is $N_g$, $$e_g(\vec{P}) = -N_g \cdot \frac{d\Phi_g}{dt} = -N_g \cdot \omega \cdot \Phi_g$$

an electromotive force is generated in the guiding coil 21 as expressed above.

As the electromotive force, a closed circuit is formed by a load impedance $Z_1$ connected to the guiding coil 21 and an impedance $R_g$ represented by a resistance component of the guiding coil 21 to cause the current to flow as described below:

$$I_g(\vec{P}) = e_g/(Z_1 + R_g)$$

to generate the second magnetic field. It is assumed here that the impedance $Z_1$ includes a resistance value $R_g$ held by the guiding coil 21.

When such a current flows in the guiding coil 21, the magnetic field strength at the position of the ith magnetic field sensor $41_i$ as descried below:

$$\vec{r}_{si} = [x_i, y_i, z_i]$$

is handled as a current element by subdividing the current flowing in the guiding coil 21, and contributions of the respective current elements are added up, and can be calculated as described below:

$$\vec{B}_{gi}(\vec{p}) = \oint \mu_0 \frac{I_g(\vec{p}) d\vec{c} \times (\vec{r}_{si} - \vec{r}_c)}{4\pi |\vec{r}_{si} - \vec{r}_c|^3}$$

as a function of P vector according to the Biot-Savart law, where $r_c$ vector represents the position of the current element.

As described above, the second magnetic field generated on the magnetic field sensor 41 due to the guiding coil 21 can be calculated with respect to one P vector representing the position and orientation of the medical device 10 having the emission coil 31 incorporated therein for generating the first magnetic field for position detection. In the first embodiment, the LUT is used for calculating the second magnetic field, and the LUT 52 is created beforehand according to the principle described above and held in the memory 51.

An outline of a method for creating the LUT 52 is explained below. In the first embodiment and embodiments described later, the LUT 52 is created based on a single filament model in which the guiding coil 21 arranged around the position detection area is approximated as one line. However, the LUT 52 can be created based on a multi-filament model in which the guiding coil 21 is approximated as a plurality of lines, or based on a coil model having a physical shape in which the guiding coil 21 is created by a finite element method. The same applies to a case that a drive coil and the emission coil arranged around the position detection area are targeted as described in the embodiments described later.

First, a target position detection area is meshed with a certain interval. Magnetic dipole moment M is arranged at respective meshed points. [mx, my, mz] can be three types of [1, 0, 0], [0, 1, 0], and [0, 0, 1]. Accordingly, three LUTs $52_x$, $52_y$, and $52_z$ are prepared for each of axes X, Y, and Z of the XYZ coordinate system with respect to position [x, y, z] of the medical device 10, and three magnetic field strengths $B_{gix}$, $B_{giy}$, and $B_{giz}$ for each axis can be acquired.

Figure 3:
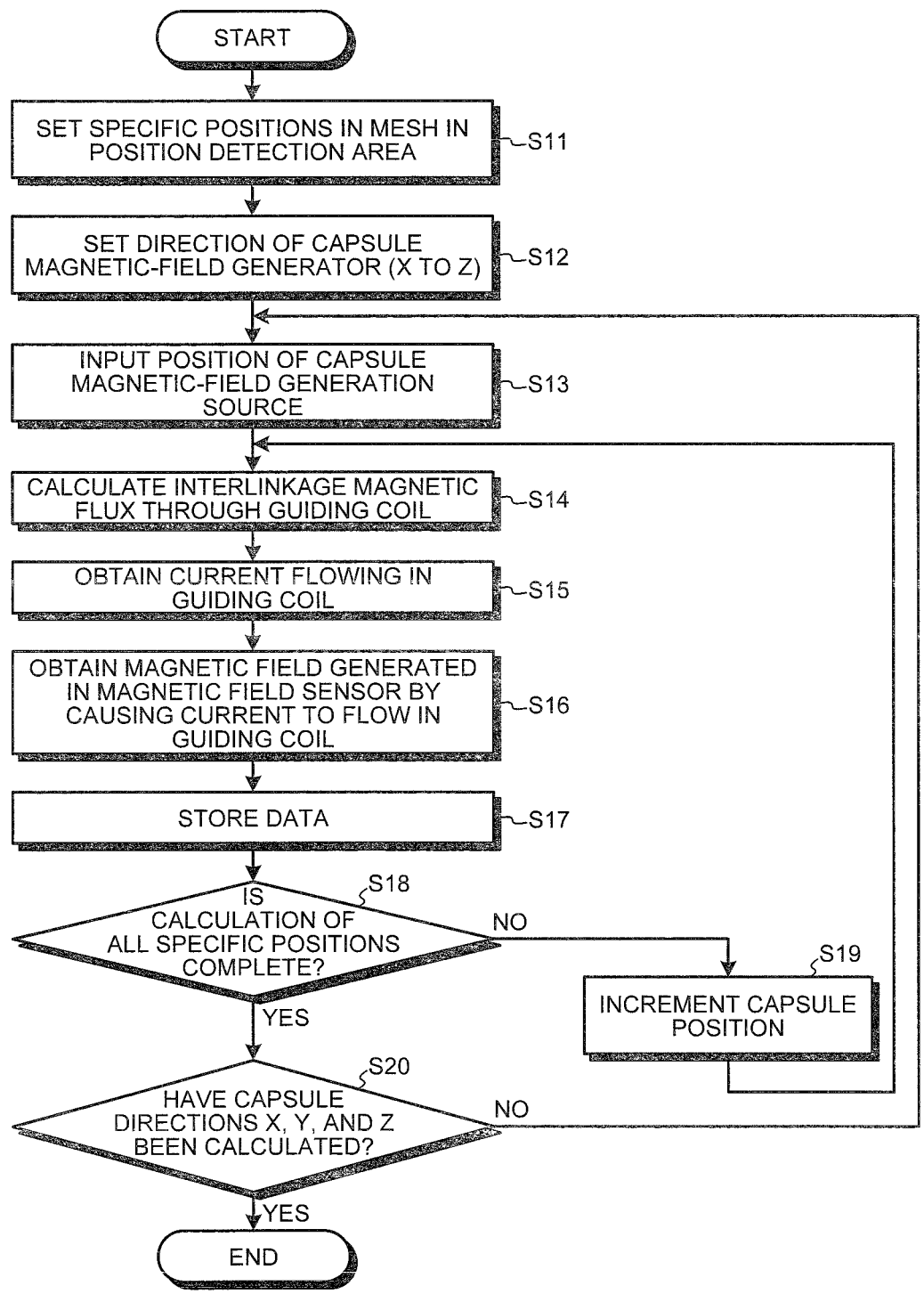
FIG. 3 is a schematic flowchart of a creating method of an LUT according to the first embodiment.

A detailed method for creating the LUTs $52_x$, $52_y$, and $52_z$ is explained with reference to a schematic flowchart shown in FIG. 3. First, a plurality of discrete specific positions are set in mesh with a predetermined interval in the position detection area for detecting the position of the medical device 10 (Step S11: specific-position setting step). The orientation of the magnetic field generator 30 (the emission coil 31) incorporated in the medical device 10 to generate the first magnetic field for position detection is set to an X-axis direction [1, 0, 0] of the target X-axis, Y-axis, and Z-axis (Step S12).

One specific position (one specific orientation is the X-axis direction) is then input as the position of the emission coil 31 (a capsule magnetic-field generation source) incorporated in the medical device 10 (Step S13). An interlinkage magnetic flux penetrating the guiding coil 21 arranged around the position detection area when the medical device 10 is positioned at the specific position and in the specific orientation to generate the first magnetic field for position detection by the emission coil 31 is calculated (Step S14: magnetic-flux calculating step). An induction current flowing in the guiding coil 21 is obtained by the calculated magnetic flux (Step S15: current calculating step). Further, the magnetic field induced to and generated at the positions of the respective magnetic field sensors $41_1$ to $41_n$ arranged around the position detection area by the guiding coil 21, when the calculated induction current flows in the guiding coil 21 is calculated as the second magnetic field (Step S16: magnetic-field calculating step). The numerical information of the calculated second magnetic field is then stored in association with the specific position and the specific orientation (Step S17: storage step).

Pieces of information of the specific positions are sequentially incremented by one until the calculation of all the specific positions is complete (NO at Step S18, Step S19: repeating step), to sequentially change the specific positions of the medical device 10, and processing at Steps S13 to S17 is repeated for all the specific positions, thereby creating the LOT $52_x$ for the X-axis in which the respective specific positions are set as variables when the orientation of the medical device 10 is in the X-axis direction.

Thereafter, the specific orientation of the magnetic field generator 30 (the emission coil 31) is sequentially set to an intended Y-axial direction [0, 1, 0] and Z-axial direction [0, 0, 1] (NO at Step S20: repeating step), and the processing from Step S13 to S19 is repeated for the Y-axis and the Z-axis in the same manner to create the LUT $52_y$ and LUT $52_z$ for the Y-axis and Z-axis in which the respective specific positions are set as variables.

Subsequently, an operation example of the position detecting device 50 using the LUT 52 is explained. The magnetic field calculator 54 acquires current estimated position information of the medical device 10 from the position calculator 56. The estimated position information is position information of a calculation start point, at the time of starting the calculation, and is position information sequentially estimated and changed each time, in middle of optimization calculation. The estimated position information is assumed as the specific position to refer to the LUTs $52_x$, $52_y$, and $52_z$, thereby calculating information of the second magnetic field generated when the medical device 10 faces a +X-axis direction, a +Y-axis direction, and a +Z-axis direction at the specific position.

Generally, it is difficult and not realistic to hold the LUT having a very large data amount, and thus the numerical information is not stored in the LUT 52 in a one-to-one relation with respect to the estimated position information. Therefore, when the estimated position of the medical device 10 is in the middle of the specific position, the magnetic field calculator 54 refers to the look-up table 52 at two specific positions putting the estimated position therebetween to calculate the second magnetic field according to linear interpolation calculation between the two specific positions, thereby obtaining the second magnetic field information with sufficient accuracy. If a coordinate pitch at the time of creating the LUT is too wide, the correction accuracy may be deteriorated. Accordingly, a pitch needs to be selected not to reduce the correction accuracy by comparing the correction data generated with a small pitch with data after interpolation.

The second magnetic field actually generated in the respective axial directions can be calculated by using $M_x$, $M_y$, and $M_z$ as the information of the magnetic dipole moment M of the medical device 10, according to an equation described below:

$$B_{gi} = B_{gix} \cdot M_x + B_{giy} \cdot M_y + B_{giz} \cdot M_z$$

The magnetic field information of the second magnetic field calculated by the magnetic field calculator 54 is output to the magnetic-field extracting unit 55. The magnetic-field extracting unit 55 subtracts second magnetic field $B_{gi}$ with respect to P vector representing the estimated position and orientation of the medical device 10 (the emission coil 31) from an actual measurement value $B_{di}$ to calculate the corrected magnetic field information obtained by correcting the actual measurement value. The position calculator 56 uses the corrected magnetic field information obtained by subtracting the second magnetic field from the actual measurement value to create an evaluation function described below:

$$\sum_{i=1}^{n} \left( \vec{B}_{di} - \vec{B}_{gi}(\vec{P}) - \vec{B}_{i}(\vec{P}) \right)^2 = 0$$

to perform optimization calculation. In the optimization calculation, because a value of P vector changes sequentially in a convergence process, the magnetic field calculator 54 refers to the LUTs $52_x$, $52_y$, and $52_z$, by using the P vector changed for each position and orientation in each case to re-calculate the second magnetic field.

The medical device guiding method according to the first embodiment performed in this manner is explained below collectively. The medical device guiding method according to the first embodiment includes: a guiding step at which a guiding magnetic field acting on the magnet 11 in the medical device 10 is generated by the guiding coil 21 supplied with power from the drive unit 24, to control the position or orientation of the medical device 10; a magnetic-field generating step at which the emission coil 31 incorporated in the medical device 10 is driven by an oscillation circuit to generate the first magnetic field of a specific frequency with respect to the position detection area; a magnetic-field detecting step at which the first magnetic field of the specific frequency is detected by a plurality of magnetic field sensors $41_1$ to $41_n$ arranged around the position detection area; and a position detecting step at which the position and orientation of the medical device 10 in the position detection area are detected based on a detection result acquired at the magnetic-field detecting step.

Figure 4:
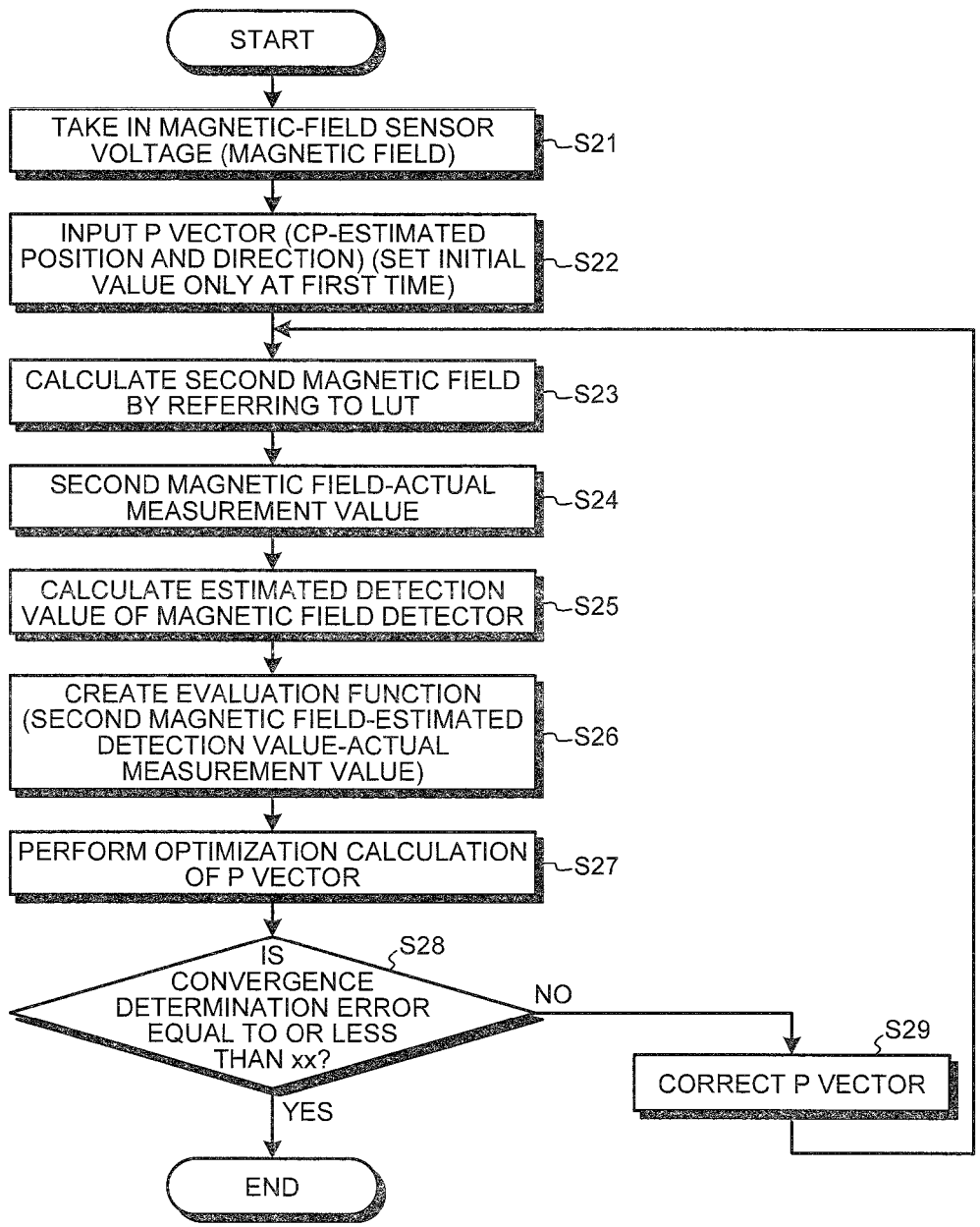
FIG. 4 is a schematic flowchart of a processing example of a position detecting step performed by a position detecting device according to the first embodiment.

A processing example of the position detecting step performed by the position detecting device 50 is shown in a schematic flowchart shown in FIG. 4. Voltage information (or magnetic field information) detected by the respective magnetic field sensors $41_1$ to $41_n$ of the magnetic field detector 40 is taken in (Step S21), and the information of P vector representing an estimated position and direction of the medical device 10 is input (Step S22). The information of P vector is set to an initial value the first time.

The magnetic field calculator 54 uses the specific position and the specific orientation represented by the P vector information as the estimated position and orientation of the medical device 10 and refers to the look-up tables $52_x$, $52_y$, and $52_z$, to calculate the second magnetic field (Step S23; magnetic-field calculating step). The magnetic-field extracting unit 55 subtracts the second magnetic field from the detected magnetic field (actual measurement value) to calculate the corrected magnetic field information (Step S24; magnetic-field extracting step). On the other hand, the position calculator 56 calculates an estimated detection value of the magnetic field to be detected by the magnetic field sensors $41_1$ to $41_n$ of the magnetic field detector 40 (Step S25), and creates an evaluation function using the corrected magnetic field information and the estimated detection value (Step S26), to perform optimization calculation of P vector by using the least-square method (Step S27). The position calculator 56 repeats such a position calculating step at Steps S25 to S27 until a convergence determination result falls within a range of equal to or less than a desired preset error xx (YES at Step S28) and repeats correction of P vector (Step S29). That is, at the position detecting step, the position and orientation of the medical device 10 are repetitively estimated until the corrected magnetic-field information calculated at Step S24 substantially matches the estimated detection value of the magnetic field calculated based on the position and orientation of the medical device 10.

According to the first embodiment, the information from the LUT 52 is additionally provided to an algorithm of the position detecting device, thereby enabling the optimization calculation. At this time, calculation of the second magnetic field comparatively takes time because of inclusion an integrating operation. However, in the first embodiment, calculation including such an integrating operation is performed beforehand and held in the memory 51 in a form of the LUT 52, thereby enabling to reduce a calculation time considerably at the time of an actual operation.

Second Embodiment

Figure 5:
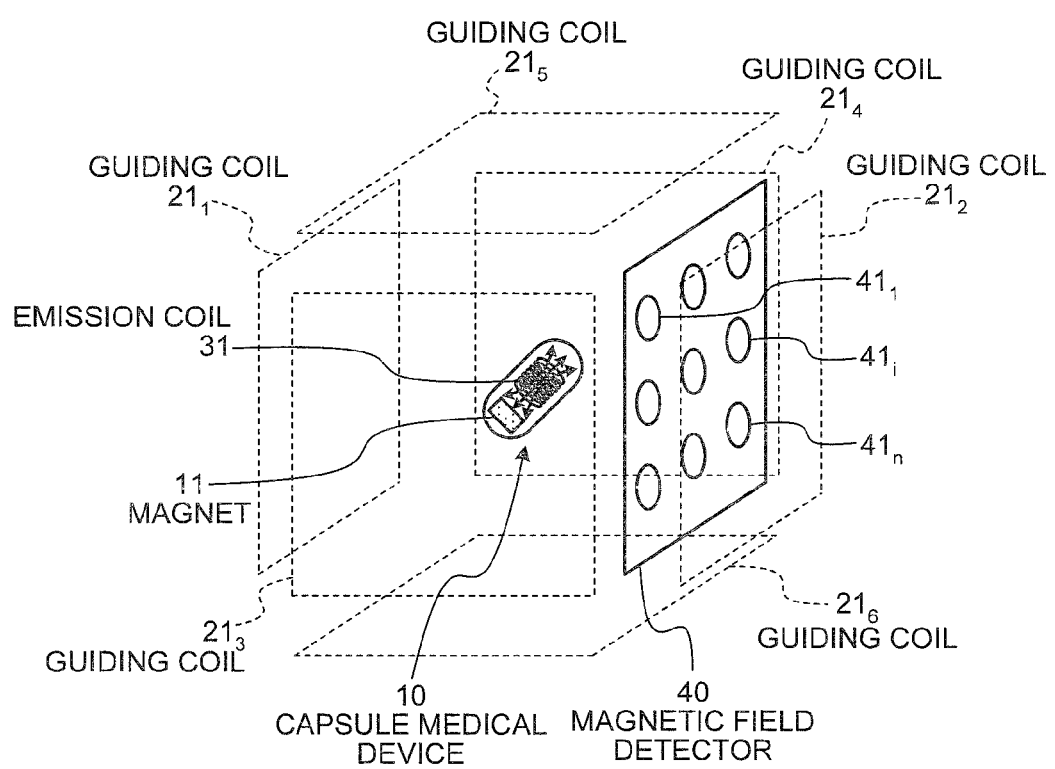
FIG. 5 is a perspective view of an example of arranging guiding coils according to a second embodiment.

A second embodiment of the present invention is explained next with reference to FIG. 5. The second embodiment relates to a method for creating the LUT, taking into consideration a more practical system configuration example in which a plurality of guiding coils are arranged.

In the drawings explaining the first embodiment, it has been explained as if the guiding coil 21 is only one. However, to guide and move the medical device 10 in an arbitrary direction in the XYZ coordinate system, in practice, several to tens of guiding coils are arranged around the position detection area to surround the position detection area. FIG. 5 is an example in which n guiding coils $21_1$ to $21_n$ (n=6) are arranged at known positions around the position detection area. In such a case, the behavior of the second magnetic field induced and generated at the positions of the magnetic field sensors $41_1$ to $41_n$ becomes more complicated.

In this case, first, as in the case described above, the first magnetic field for position detection generated by the emission coil 31 incorporated in the medical device 10 acts on the respective guiding coils $21_1$ to $21_n$ to guide and generate the second magnetic field respectively. In a phenomenon heretofore, the magnetic field strength in the magnetic field detector 40 is calculated as an influence of the medical device 10 with respect to the respective guiding coils $21_1$ to $21_n$ respectively, and these are added up lastly.

In practice, however, the guided respective guiding coils $21_1$ to $21_n$ become a new magnetic-field generation source, to cause multiple interference such that the second magnetic field is guided and generated with respect to other remaining guiding coils. The second magnetic field occurs with a phase opposite to that of the first magnetic field, which is a cause, and the magnetic field strength becomes smaller. Accordingly, the calculation method is repeated to finally reach certain equilibrium. Therefore, the LUT 52 can be created by determining up to which order of the multiple interference is taken into consideration according to the accuracy required for the position detecting device 50.

Third Embodiment

A third embodiment of the present invention is explained next with reference to FIG. 6. The third embodiment relates to another method for creating the LUT, taking into consideration multiple interference of the guiding coil 21 as explained in the second embodiment. The third embodiment focuses on a point that guidance between the coils can be represented by defining mutual inductance between the coils.

First, an identification number i, j=1, 2, ..., or n is added to each of n guiding coils $21_1$ to $21_n$, and number 0 is added to the emission coil 31 incorporated in the medical device 10, thereby defining the mutual inductance between the coils. Subscripts i, j mean that it is the mutual inductance between the ith coil and the jth coil. It is assumed that a direction affected by the magnetic field is i←j. However, $L_{ij}$ and $L_{ji}$ are the same. According to the definition, i=j is also possible, which generally represents self inductance; however, it is not particularly distinguished here.

Under such conditions, the mutual inductance is determined according to a physical shape and arrangement of the coils. More specifically, the mutual inductance represents the number of magnetic fluxes which interlink with the other coil when a unitary current is caused to flow in one coil. Therefore, the magnetic flux passing through other guiding coils $21_1$ to $21_n$ when a current $I_0=1A$ is caused to flow in the emission coil 31 incorporated in the medical device 10 is obtained. That is, mutual inductance $L_{i0}$ to be obtained here is substantially the same as that obtained in the case of passing magnetic-flux calculation explained in the first embodiment. The magnetic dipole moment N is expressed by $\mu_0 * I_0 * S_0 * N_0$ ($\mu_0$: permeability, $S_0$: cross section of the coil, $N_0$: number of turns of the coil). Therefore, the difference from the first embodiment is that conversion is required and the number of turns $N_i$ of the targeted coil i is multiplied. Three values can be calculated with respect to one specific position of the medical device 10, designating the orientation of the medical device 10 as coordinate axes +X, +Y, +Z.

The mutual inductances between respective guiding coils $21_1$ to $21_n$ are prepared. The arrangement position of the guiding coil 21 is generally fixed and known. Therefore, n×n matrix can be prepared with respect to n guiding coils $21_1$ to $21_n$. To simplify the explanation, a case of n=4 (i,j=1 to 4) is assumed here (it is irrelevant to whether the case is established as the position detecting device). First, when voltage generated in the first guiding coil $21_1$ is obtained, it becomes as described below with respect to i=1:

$$V_1 = -L_{10} \cdot \frac{dI_0}{dt} - L_{11} \cdot \frac{dI_1}{dt} - L_{21} \cdot \frac{dI_2}{dt} - L_{31} \cdot \frac{dI_3}{dt} - L_{41} \cdot \frac{dI_4}{dt} = I_1 \cdot Z_1$$

Likewise, four expressions as described below:

$$V_i = -L_{i0} \cdot \frac{dI_0}{dt} - \sum_{j=1}^{4} L_{ij} \cdot \frac{dI_j}{dt} = I_i \cdot Z_i$$

are established with respect to the ith guiding coil $21_1$. If it is assumed that the first magnetic field for position detection is individually a sine wave of angular frequency ω[rad], a term of dI/dt becomes ωI.

To summarize these expressions, they are represented conceptually by the following expression in a matrix notation:

$$I = -I_0[L + Z_1/j\omega]^{-1} \cdot L_0$$

L denotes a mutual inductance matrix between the guiding coils, $L_0$ denotes the mutual inductance matrix between the emission coil 31 in the medical device 10 and the guiding coils $21_1$ to $21_n$, and j denotes an imaginary unit. When the guiding coils $21_1$ to $21_n$ are connected to a drive amplifier, $I_i * Z_i$ in right term can be handled as 0. That is, by calculating the following expression:

$$I = -I_0[L]^{-1} \cdot L_0$$

Thus, the current flowing in respective coils of I matrices $I_1$ to $I_k$ can be obtained.

An operation for obtaining the current is to calculate individual values such as $I_x$, $I_y$, and $I_z$ with respect to the three directions (directions of +X, +Y, and +Z) of the magnetic field generator 30 (the emission coil 31). The second magnetic field generated at the positions of magnetic field sensors $41_1$ to $41_n$ when the current is caused to flow in the guiding coils $21_1$ to $21_n$, respectively, can be obtained as explained in the first embodiment.

Therefore, three pieces of numerical information $B_x$, $B_y$, and $B_z$ associated with the second magnetic field can be obtained, in which the position information of the medical device 10 is designated as a variable, according to the method described above, thereby enabling to create LUTs $52_x$, $52_y$, and $52_z$.

Figure 6:
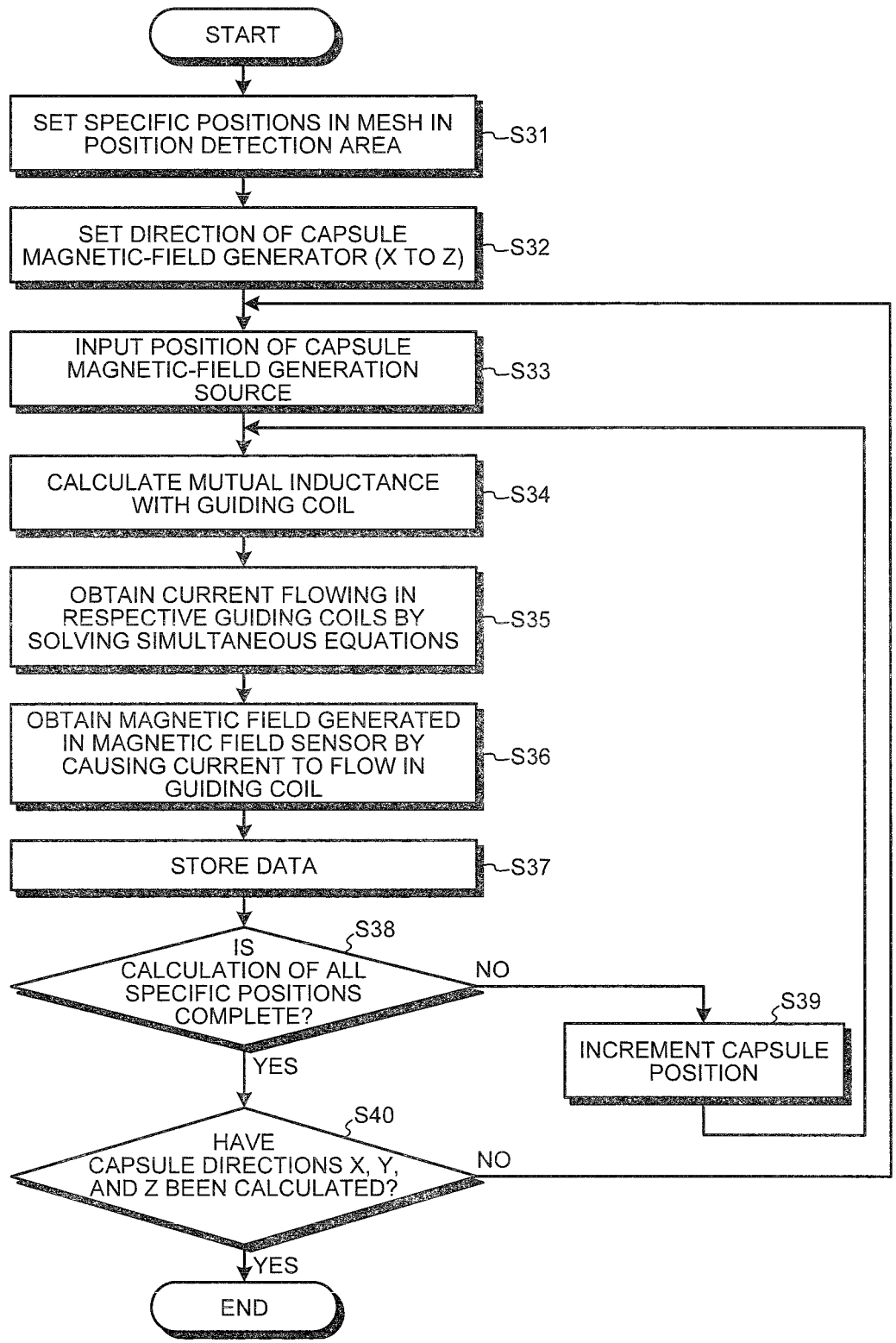
FIG. 6 is a schematic flowchart of a creating method of an LUT according to a third embodiment.

A method for creating the LUTs $52_x$, $52_y$, and $52_z$ according to the third embodiment, using the mutual inductance, is collectively shown in a schematic flowchart in FIG. 6. In the flowchart shown in FIG. 6, in a part for obtaining the current, it is assumed that the mutual inductance between the guiding coils is known beforehand. First, a plurality of discrete specific positions are set in mesh with a predetermined interval in the position detection area for detecting the position of the medical device 10 (Step S31: specific-position setting step). The orientation of the magnetic field generator 30 (the emission coil 31) incorporated in the medical device 10 to generate the first magnetic field for position detection is set to an X-axis direction [1, 0, 0] of the targeted X-axis, Y-axis, and Z-axis (Step S32).

Next, one specific position (one specific orientation is the X-axis direction) is input as the position of the emission coil 31 (capsule magnetic-field generation source) incorporated in the medical device 10 (Step S33). The mutual inductance with the guiding coil is calculated (Step S34: mutual-inductance calculating step). The induction current flowing in the guiding coil 21 is obtained by solving simultaneous equations associated with the voltage generated in each guiding coil (Step S35: current calculating step). The magnetic field induced and generated at the positions of the respective magnetic field sensors $41_1$ to $41_n$ arranged around the position detection area when the calculated induction current flows in the guiding coil is calculated as the second magnetic field (Step S36: magnetic-field calculating step). The numerical information of the calculated second magnetic field is stored in association with the specific position and the specific orientation (Step S37: storage step).

Pieces of information of the specific positions are sequentially incremented by one until the calculation of all the specific positions is complete (NO at Step S38, Step S39: repeating step), to sequentially change the specific positions, and processing at Steps S33 to S37 is repeated for all the specific positions, thereby creating the LUT $52_x$ for the X-axis in which the respective specific positions are set as variables.

Thereafter, the orientation of the magnetic field generator 30 (the emission coil 31) is sequentially set to the target Y-axial direction [0, 1, 0] and Z-axial direction [0, 0, 1] (NO at Step S40: repeating step), and the processing from Step S33 to S39 is repeated for the Y-axis and the Z-axis in the same manner to create the LUT $52_y$ and LUT $52_z$ for the Y-axis and Z-axis in which the respective specific positions are set as variables.

In the third embodiment, the magnetic field calculator 54 obtains a value of the second magnetic field by using the numerical information of the LUTs $52_x$, $52_y$, and $52_z$ and the current value of the magnetic dipole moment M. That is, the second magnetic field becomes:

$$B_{gi} = (B_{ix} * M_x / |M| + B_{iy} * M_y / |M| + B_{iz} * M_z / |M|) * I_0.$$

In the method of the third embodiment, because the current is obtained after the simultaneous equations of generated voltage are once established, a solution thereof means the equilibrium, and thus an order of interference does not need to be specified.

As a modification of the third embodiment, the mutual inductance (including self inductance) can be obtained by creating the LUT by using a value actually measured by the device. Specifically, the mutual inductance can be obtained from a result of actually causing the current to flow in a certain coil and measuring an electromotive force generated by the other remaining coils. A mechanism for generating the electromotive force is as explained in the first embodiment.

Fourth Embodiment

Figure 7:
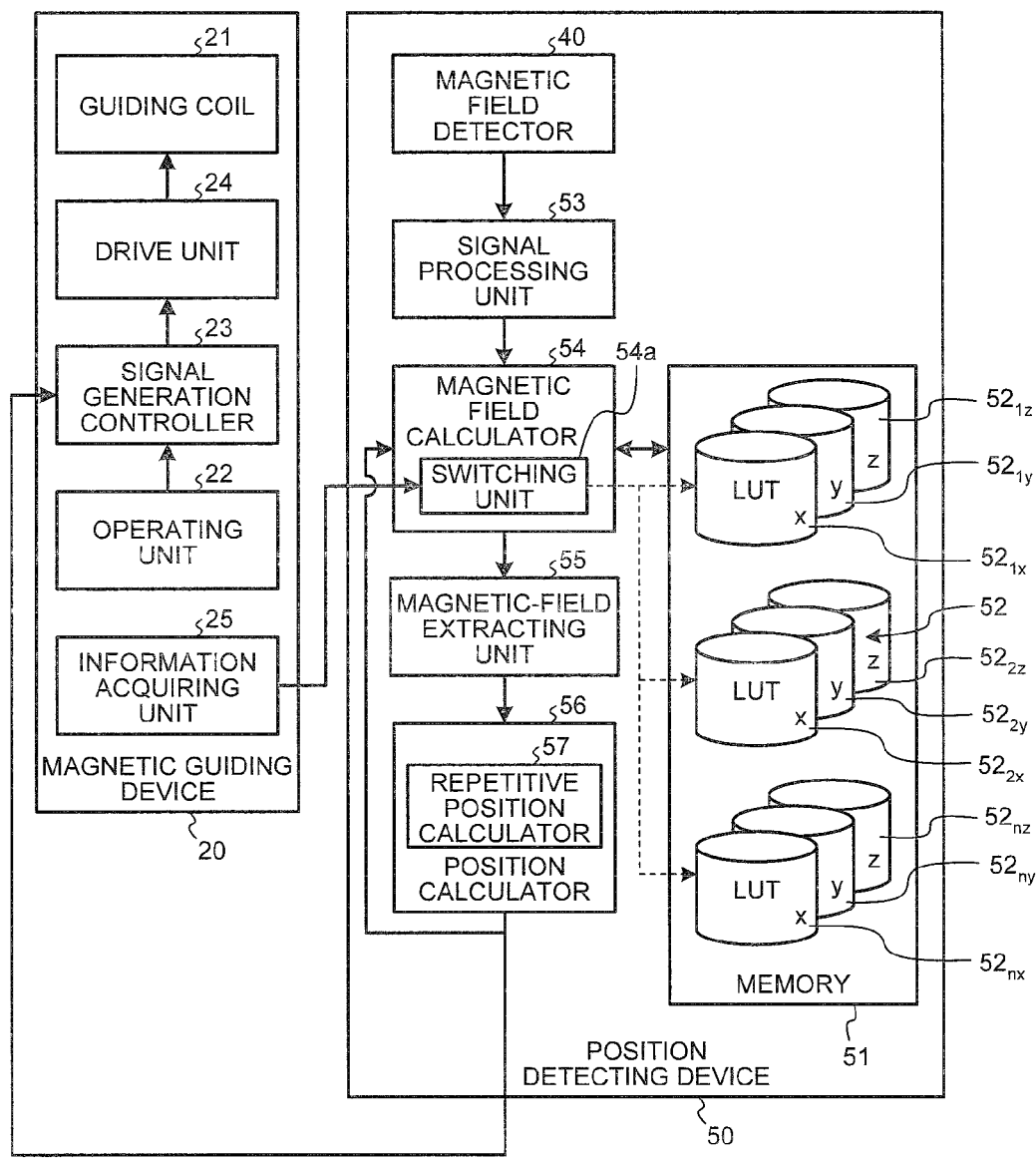
FIG. 7 is a schematic block diagram of a configuration example of a medical device guiding system according to a fourth embodiment.
Figure 8:
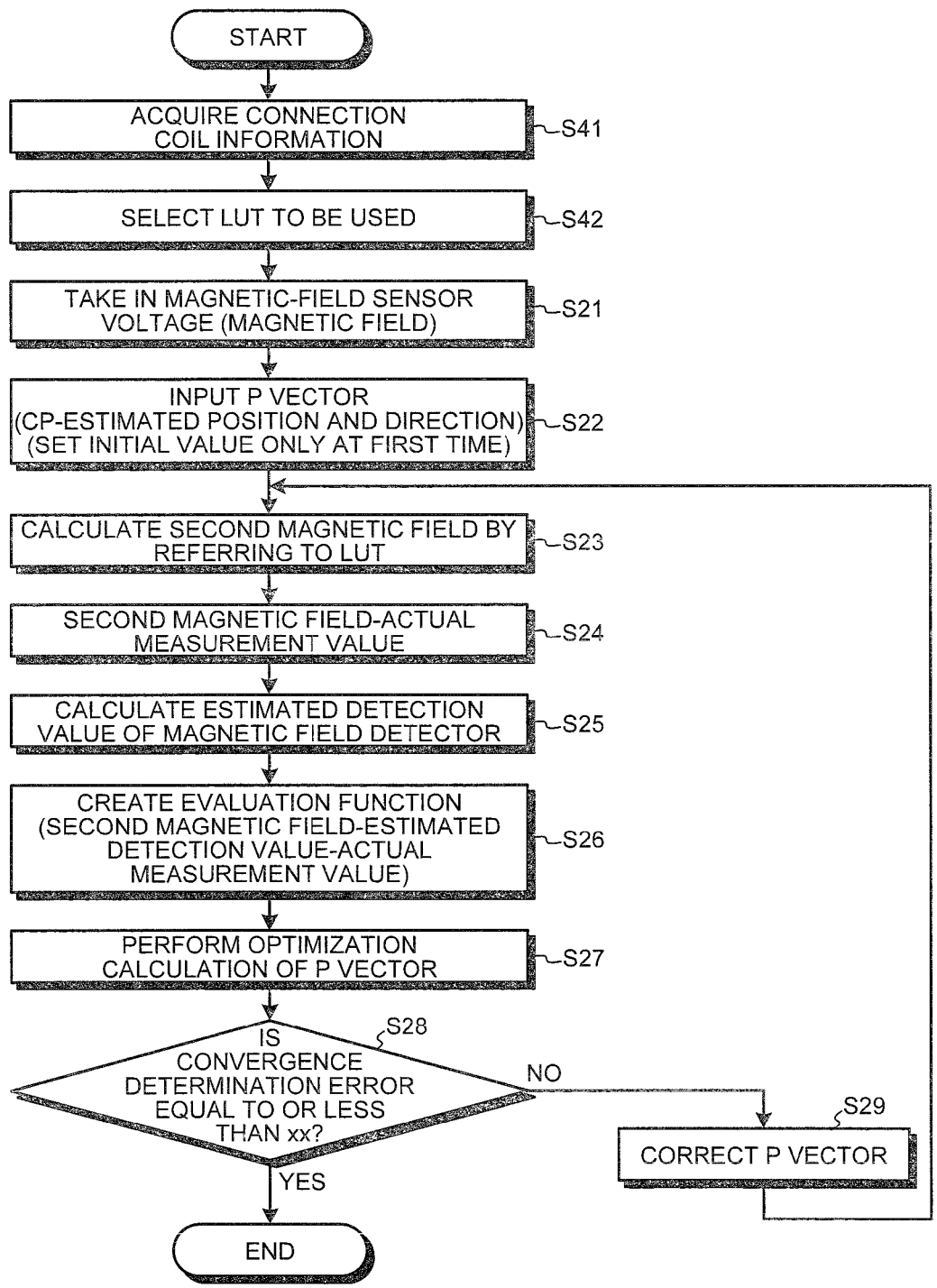
FIG. 8 is a schematic flowchart of a processing example of a position detecting step performed by a position detecting device according to the fourth embodiment.

A fourth embodiment of the present invention is explained with reference to FIG. 7 and FIG. 8. FIG. 7 is a schematic block diagram of a configuration example of a medical device guiding system according to the fourth embodiment. FIG. 8 is a schematic flowchart of a processing example of a position detecting step performed by the position detecting device 50 according to the fourth embodiment. In the fourth embodiment, a change of the connection condition of the guiding coils $21_1$ to $21_n$ is taken into consideration. That is, in the third embodiment or the like, calculation is performed assuming that the impedance connected to the guiding coils $21_1$ to $21_n$ is 0 in a calculation process of the LUT 52. However, an influence of the impedance change may be large because of being used in such a state that a certain unused guiding coil $21_i$ is electrically detached. Electrical detachment of the guiding coil $21_i$ means that the impedance becomes infinite, and because the current does not flow in the guiding coil $21_i$, there is no influence thereof (the second magnetic field is not generated by the guiding coil $21_i$).

In the fourth embodiment, as shown in FIG. 7, LUTs $52_{1x}$, $52_{1y}$, $52_{1z}$, $52_{2x}$, $52_{2y}$, $52_{2z}$, . . . , $52_{nx}$, $52_{ny}$, and $52_{nz}$ grouped into n types different for each connection mode of the guiding coils $21_1$ to $21_n$ are created and held in the memory 51, and the group of the LUT 52 to be referred to according to the connection mode of the guiding coils $21_1$ to $21_n$ is switched. The information of the connection mode of the guiding coils $21_1$ to $21_n$ is recognized by an information acquiring unit 25 added to the magnetic guiding device 20, and is output to a switching unit 54a provided in the magnetic field calculator 54 of the position detecting device 50. The switching unit 54a obtains the information of the connection mode from the information acquiring unit 25 to switch the group of the LUT 52 to be referred to by the magnetic field calculator 54.

The position detecting step in the fourth embodiment is explained with reference to FIG. 8. Basically, the position detecting step in the fourth embodiment is the same as the processing example of the position detecting step shown in FIG. 4. However, in the fourth embodiment, as preprocessing at the magnetic-field calculating step, connection coil information is acquired as the information of the connection mode of the guiding coils $21_1$ to $21_n$ from the information acquiring unit 25 of the magnetic guiding device 20 (Step S41), and the switching unit 54a first performs processing for selecting a group of the LUT 52 to be used according to the connection coil information (Step S42; table switching step) to perform processing at Step S21 and thereafter by using the LUT 52 of the selected group.

Fifth Embodiment

Figure 9:
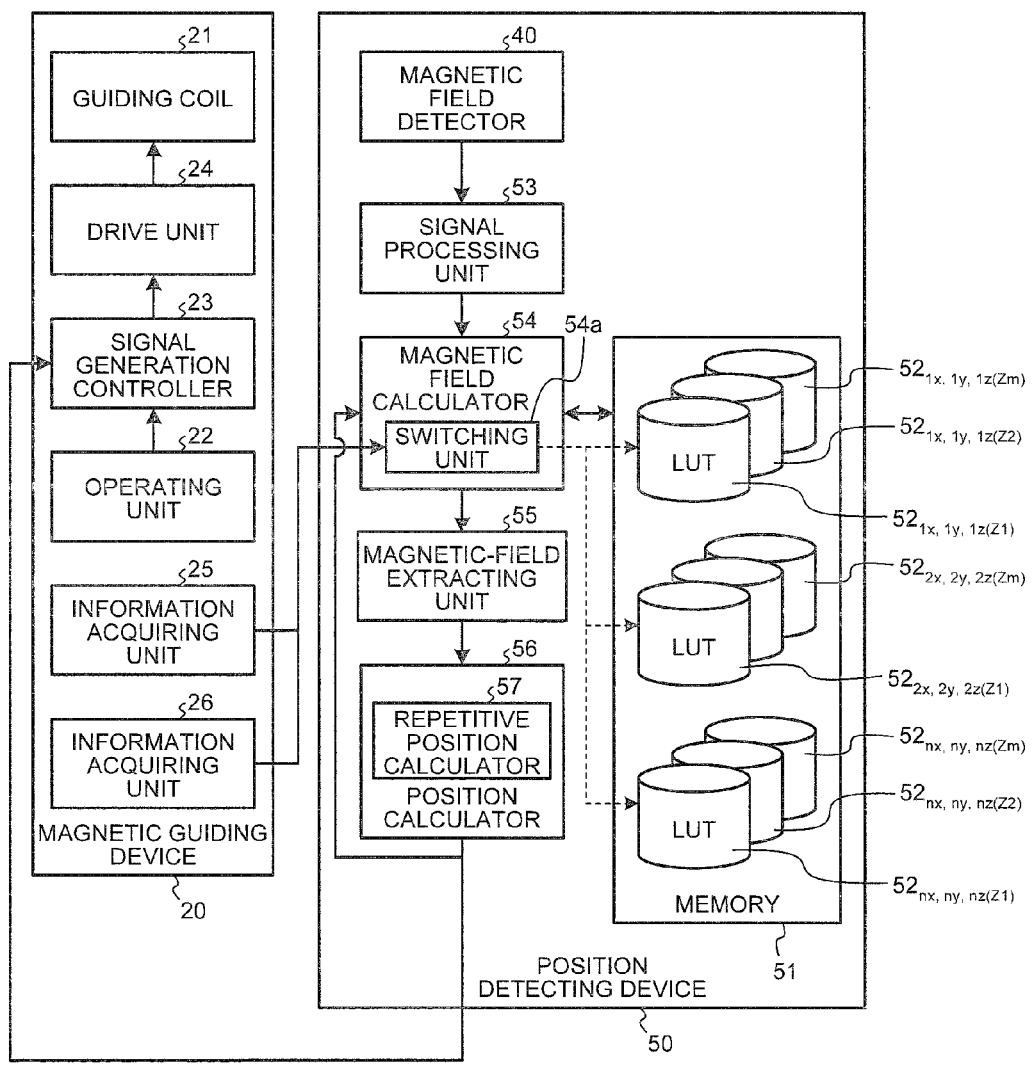
FIG. 9 is a schematic block diagram of a configuration example of a medical device guiding system according to a fifth embodiment.
Figure 10:
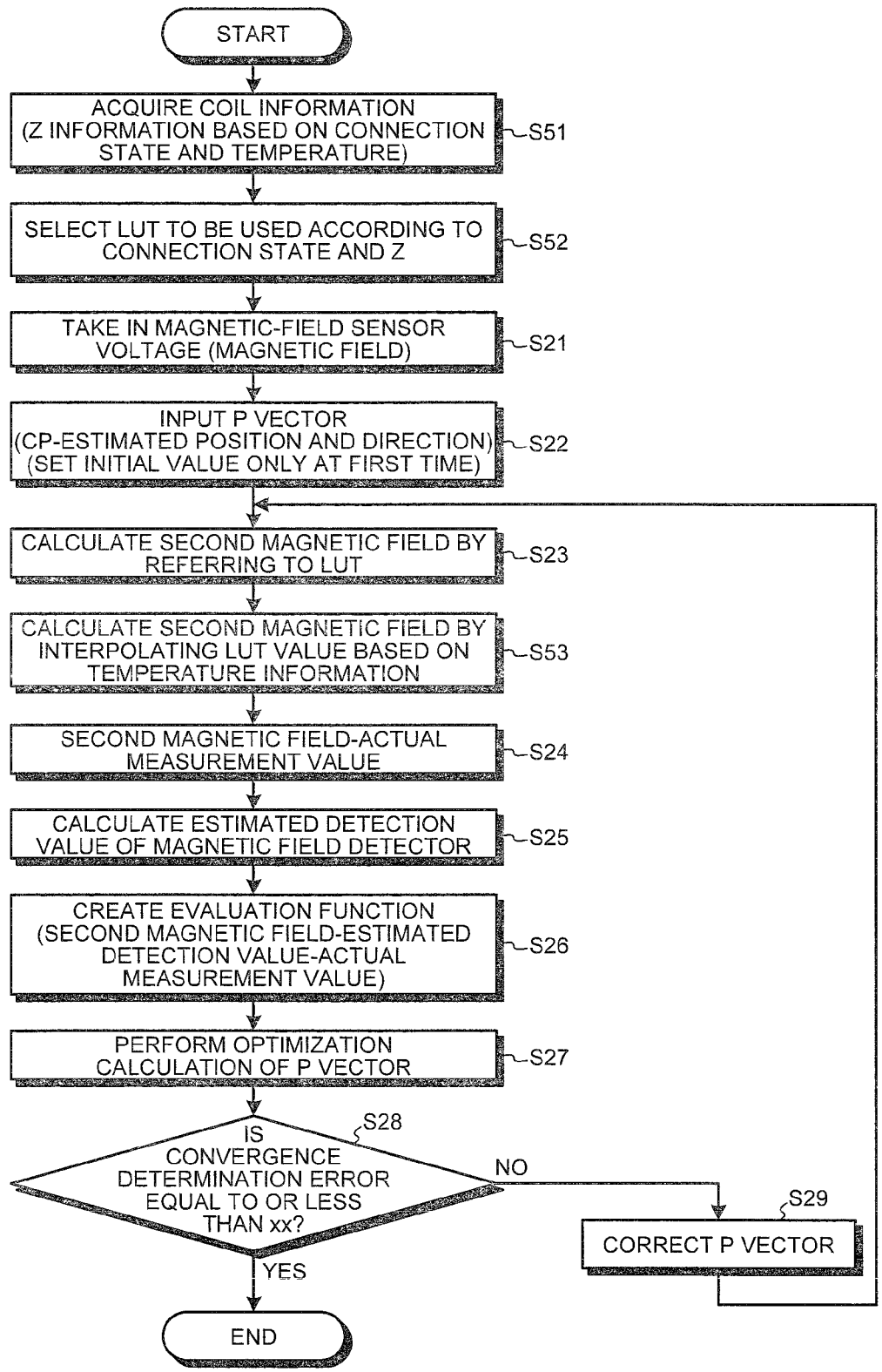
FIG. 10 is a schematic flowchart of a processing example of a position detecting step performed by a position detecting device according to the fifth embodiment.

A fifth embodiment of the present invention is explained next with reference to FIG. 9 and FIG. 10. FIG. 9 is a schematic block diagram of a configuration example of the medical device guiding system according to the fifth embodiment and FIG. 10 is a schematic flowchart of a processing example of the position detecting step performed by the position detecting device 50 according to the fifth embodiment. The fifth embodiment takes into consideration an impedance change with a change of the connection mode of the guiding coils $21_1$ to $21_n$ and a temperature change. That is, in the fourth embodiment, the group of the LUT 52 to be referred to is switched, taking into consideration a case that the impedance to be connected to the guiding coils $21_1$ to $21_n$ is 0 or infinite. However, the guiding coil 21 can indicate a continuous change such that a value of resistance (impedance) of the coil changes due to a temperature change.

In the fifth embodiment, therefore, as shown in FIG. 9, when the LUIS $52_{1x,1y,1z}$, $52_{2x,2y,2z}$, . . . , and $52_{nx,ny,nz}$ of different n types grouped for each connection mode of the guiding coils $21_1$ to $21_n$ are created beforehand (for example, subscript $1x$, $1y$, and $1z$ is used to express three types in one together), LUTs $52_{1x,1y,1z}(Z1)$, $52_{1x,1y,1z}(Z2)$, . . . , $52_{1x,1y,1z}(Zm)$, $52_{2x,2y,2z}(Z1)$, $52_{2x,2y,2z}(Z2)$, $52_{2x,2y,2z}(Zm)$, . . . , $52_{nx,ny,nz}(Z1)$, $52_{nx,ny,nz}(Z2)$, and $52_{nx,ny,nz}(Zm)$ at representative m-type specific impedances Z1, Z2, . . . , Zm are created and held in the memory 51 in the respective groups, to switch the LUT 52 to be referred to according to the impedance information based on the information of the connection mode of the guiding coils $21_1$ to $21_n$ and the coil temperature. The information of the connection mode of the guiding coils 211 to 21*n* is recognized by the information acquiring unit 25 added to the magnetic guiding device 20, and the impedance information based on the temperature of the guiding coil 21 is recognized by an information acquiring unit 26 added to the magnetic guiding device 20, and output to the switching unit 54a provided in the magnetic field calculator 54 of the position detecting device 50. The switching unit 54a acquires the information of the connection mode and the impedance information from the information acquiring unit 25 to switch the group of the LUT 52 to be referred to by the magnetic field calculator 54.

The position detecting step in the fifth embodiment is explained with reference to FIG. 10. Basically, the position detecting step in the fifth embodiment is the same as the processing example of the position detecting step shown in FIG. 4. However, in the fifth embodiment, as preprocessing at the magnetic-field calculating step, connection coil information and impedance Z information based on the coil temperature are acquired as the information of the connection mode of the guiding coils $21_1$ to $21_n$ from the information acquiring units 25 and 26 of the magnetic guiding device 20 (Step S51), and the switching unit 54a selects a group of the LUT 52 to be used according to the connection coil information and the impedance Z information (Step S52) to perform processing at Step S21 and thereafter by using the LUT 52 of the group corresponding to a selected impedance.

Because the LUT 52 is created according to representative specific impedances Z1, Z2, . . . , Zm, the acquired impedance information may not match these specific impedances Z1, Z2, . . . , Zm. In this case, the second magnetic fields thereof is respectively calculated by referring to the LUT 52 of two specific impedances putting the acquired impedance therebetween, to perform linear interpolation calculation between the two specific impedances (Step S53), thereby enabling to calculate the second magnetic field corresponding to the coil impedance based on the coil temperature.

Sixth Embodiment

Figure 11:
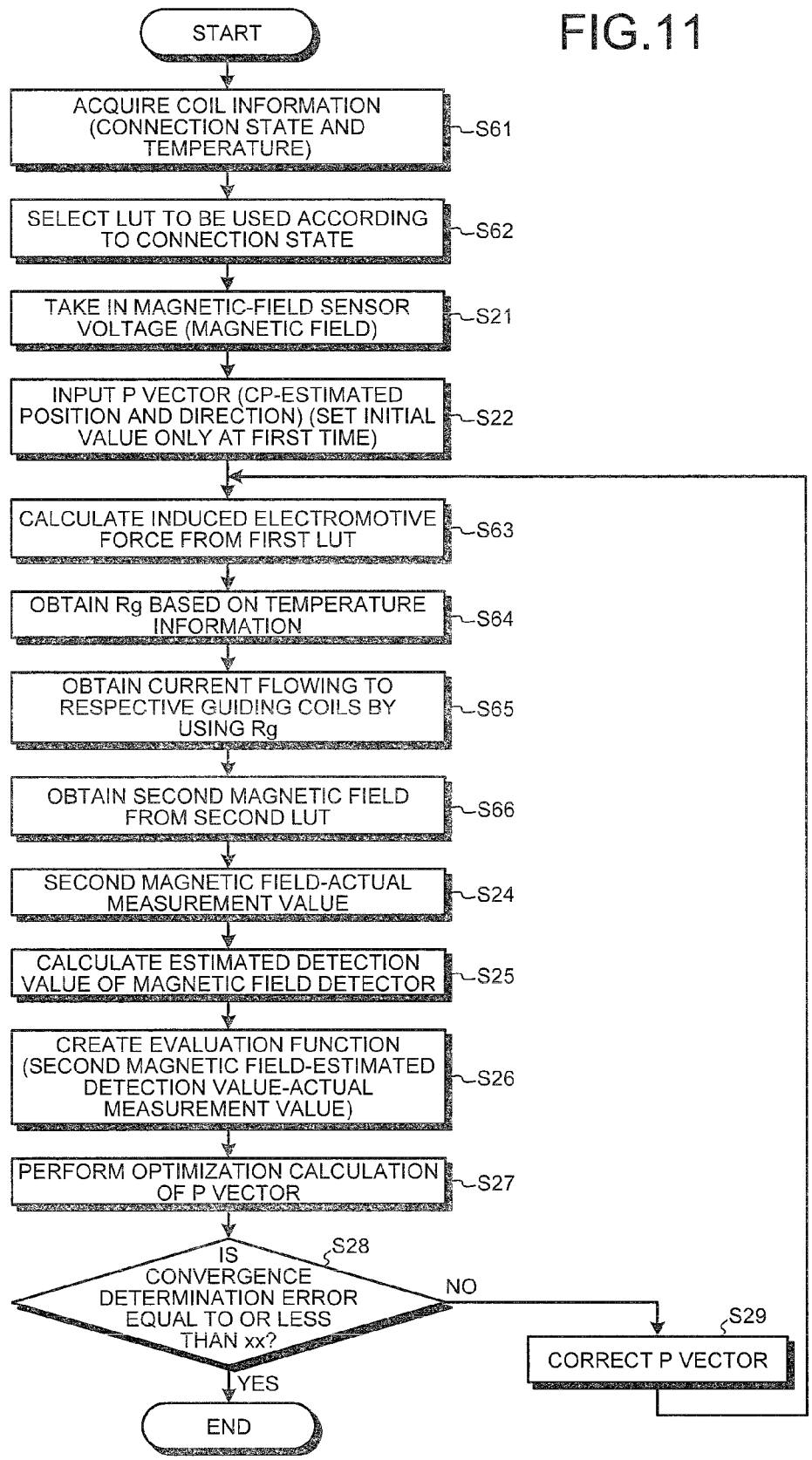
FIG. 11 is a schematic flowchart of a processing example of a position detecting step performed by a position detecting device according to a sixth embodiment.

Subsequently, a sixth embodiment of the present invention is explained with reference to FIG. 11. FIG. 11 is a schematic flowchart of a processing example of the position detecting step performed by the position detecting device 50 according to the sixth embodiment. The sixth embodiment takes into consideration a case that an impedance change with a change of coil temperature is complicated and it is difficult to perform the linear interpolation calculation. That is, in the fifth embodiment, a case that the impedance connected to the guiding coils $21_1$ to $21_n$ is 0 or infinite (there is no unnecessary magnetic field) and the impedance of the coil are taken into consideration to switch the LUT 52, and the linear interpolation is performed between the LUTs 52 according to the coil impedance. However, when the impedance change with the temperature change of the guiding coil is complicated, the linear interpolation may not be simple. Because resistance (impedance) of copper forming the coil is changed according to the temperature of the guiding coil 21, the value of an impedance $Z_g$ connected to the guiding coil 21 can be calculated (estimated) by calculation.

Further, in the third embodiment, the second magnetic field generated at the position of the magnetic field sensor 41 is calculated at a time based on the position and orientation of the medical device 10 by using the LUT 52. However, in the sixth embodiment, the LUT 52 is configured by being divided into a first LUT in which numerical information having a correlation with the current flowing in the guiding coil 21 due to guidance by the magnetic field generator 30 is stored, designating the position information of the magnetic field generator 30 as a variable, and a second LUT in which numerical information having the correlation with the second magnetic field induced and generated at the position of the magnetic field detector 40 when a preset specific current is caused to flow in the guiding coil 21 is stored, designating the position information of the magnetic field detector 40 as a variable. The magnetic field calculator 54 calculates the current flowing in the guiding coil 21 by using the numerical information acquired by referring to the first LUT based on the position information of the magnetic field generator 30 and the impedance information, and calculates the second magnetic field by referring to the second LUT based on the calculated current. That is, the first LUT is used for a part for obtaining the current flowing in the guiding coil 21, and an impedance $Z_1$ calculated based on coil temperature information acquired from the information acquiring unit 26 is input each time to solve a matrix, thereby obtaining the second magnetic field by referring to the second LUT using the obtained current.

The position detecting step in the sixth embodiment is explained with reference to FIG. 11. First, the connection coil information and coil temperature information are acquired as the information of the connection mode of the guiding coils $21_1$ to $21_n$ from the information acquiring units 25 and 26 of the magnetic guiding device 20 (Step S61), and the switching unit 54a selects a group of the LUT 52 to be used according to the connection coil information (Step S62). The voltage information (or magnetic field information) detected by the respective guiding coils $21_1$ to $21_n$ of the magnetic field detector 40 is taken in (Step S21), and the information of P vector representing an estimated position and orientation of the medical device 10 is input (Step S22). The information of P vector is set to an initial value the first time.

The magnetic field calculator 54 refers to the first LUT by using the specific position represented by the P vector information indicating the estimated position of the medical device 10 to calculate induced electromotive force (Step S63). The magnetic field calculator 54 further calculates a resistance $R_g$ of the guiding coil 21 based on the coil temperature information acquired from the information acquiring unit 26 (Step S64), and calculates a current $I_g$ flowing in the respective guiding coils $21_1$ to $21_n$ based on the calculated resistance $R_g$ and the inductance of the guiding coil 21 (Step S65).

$$I_g(\vec{P}) = e_g/(Z_1 + R_g)$$

The second magnetic field generated on the magnetic field sensor 41 is then calculated by referring to the second LUT based on the calculated current $I_g$ (Step S66). Thereafter, the processing at Steps S24 to S29 is repeated as in the case shown in FIG. 4.

When the LUT is created by using the mutual inductance as shown in FIG. 6, mutual inductance $L_0$ between the emission coil 31 incorporated in the medical device 10 and the guiding coil 21 is calculated by referring to the first LUT, using the specific position represented by the P vector information indicating the estimated position of the medical device 10. A matricial equation is created by substituting the resistance $R_g$ calculated based on the coil temperature information, and the matricial equation is solved, thereby obtaining a current I flowing in the guiding coil 21 as described below:

$$I = -I_0[L + R_g/j\omega]^{-1} \cdot L_0$$

The unnecessary magnetic field generated on the magnetic field sensor 41 can be calculated by referring to the second LUT based on the calculated current I.

Seventh Embodiment

Figure 12:
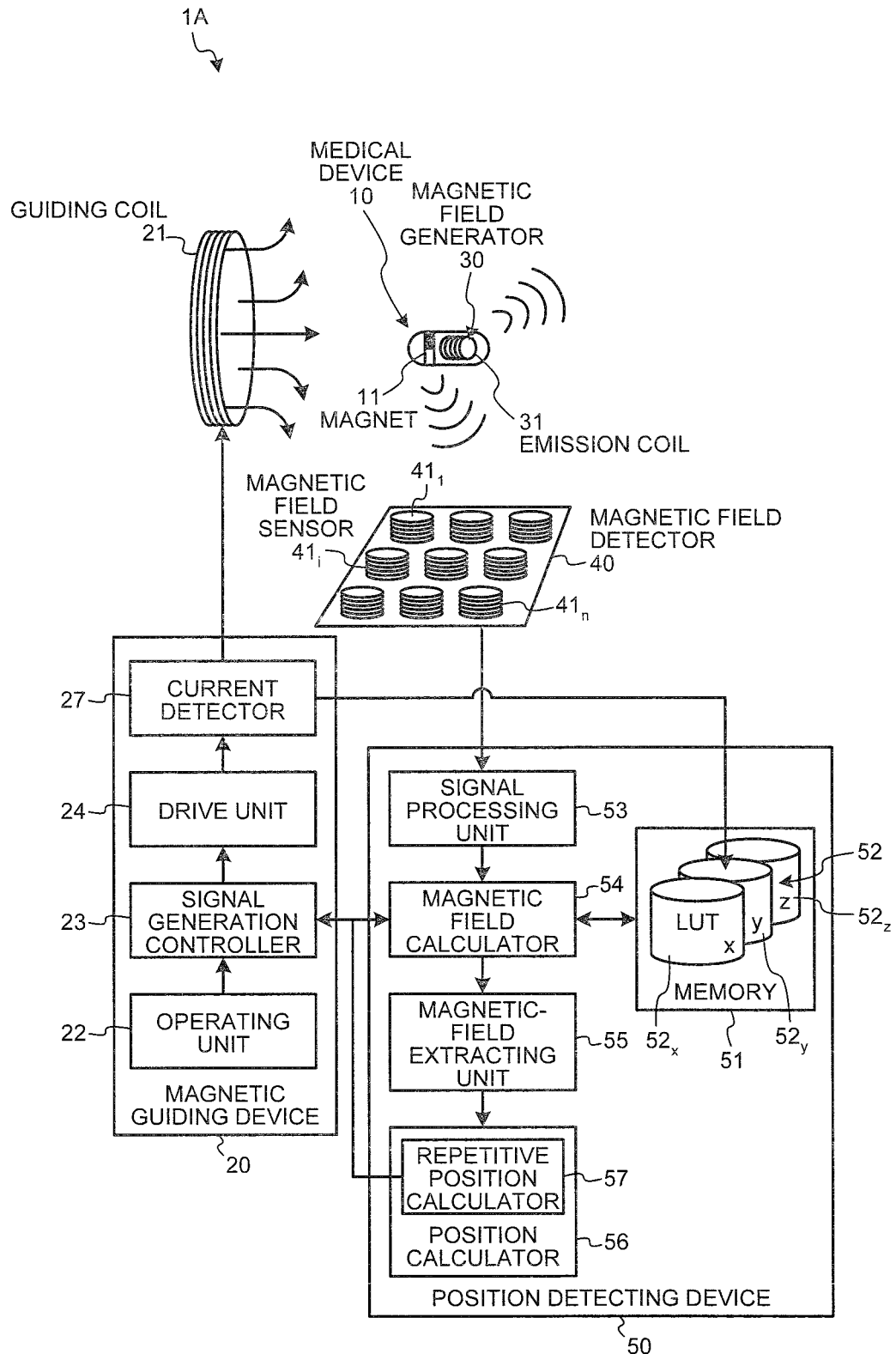
FIG. 12 is a schematic diagram of a fundamental configuration example of a medical device guiding system according to a seventh embodiment.

A seventh embodiment of the present invention is explained with reference to FIG. 12. In the explanation described above, the LUT 52 is created based on calculation. However, in the seventh embodiment, a part of the LUT 52 is created by using actual measurement data, which can be applied to embodiments described later.

In the seventh embodiment, a current detector 27 that detects the current flowing in the guiding coil 21 is provided in the magnetic guiding device 20. An actually measured current value detected by the current detector 27 is input to the LUT 52 in the position detecting device 50, thereby obtaining the second magnetic field. When a predetermined current is caused to flow in the guiding coil 21, the second magnetic field generated at the position of the magnetic field sensor 41 can be obtained by referring to the LUT 52 based on the current value.

Eighth Embodiment

Figure 13:
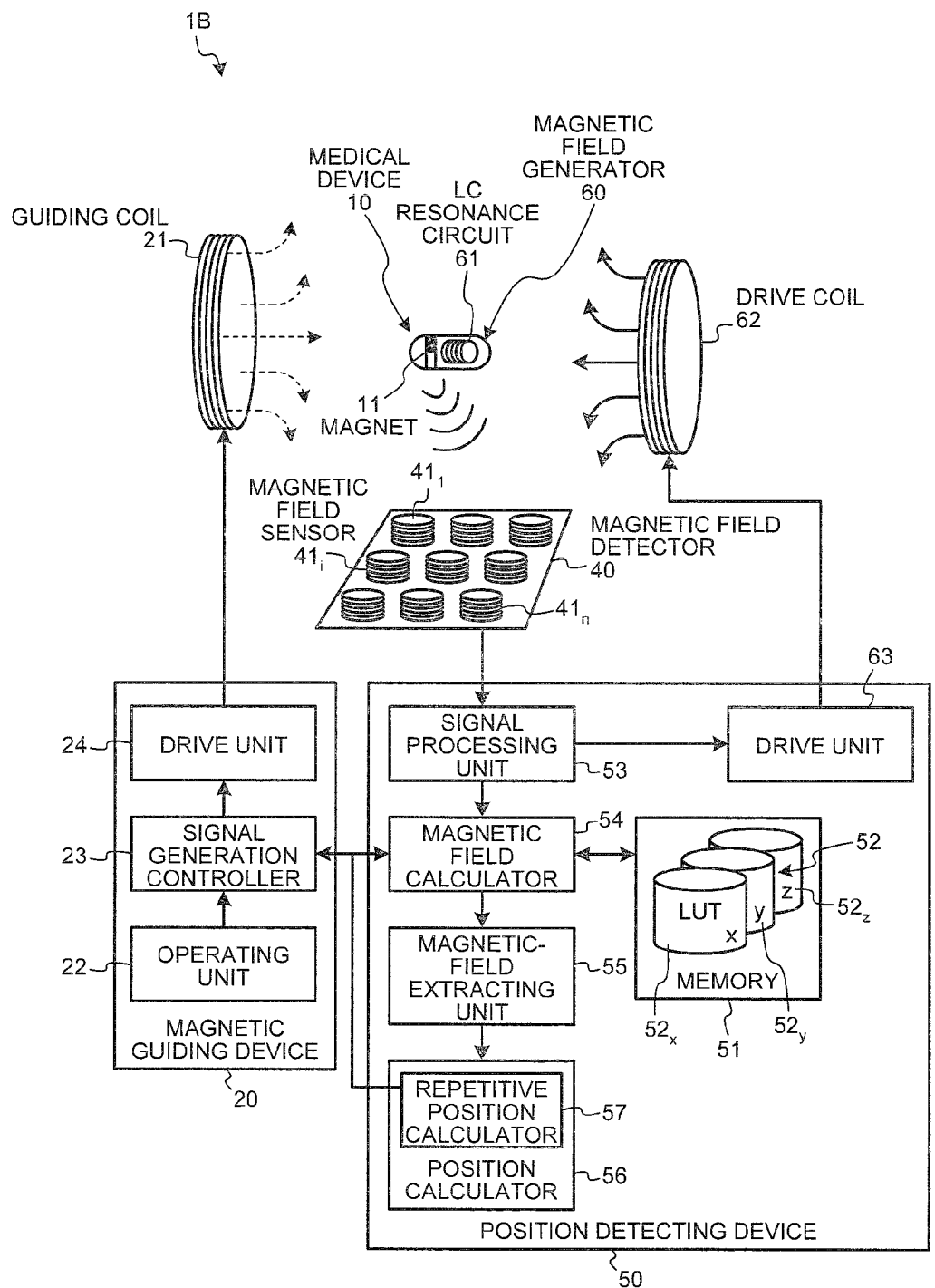
FIG. 13 is a schematic diagram of a fundamental configuration example of a medical device guiding system according to an eighth embodiment.

An eighth embodiment of the present invention is explained with reference to FIG. 13. FIG. 13 is a schematic diagram of a fundamental configuration example of a medical device guiding system according to the eighth embodiment of the present invention. In a medical device guiding system 1B according to the eighth embodiment, the position detecting device 50 includes an inductive magnetic field generator 60 instead of the magnetic field generator 30. The magnetic field generator 60 includes an LC resonance circuit 61 incorporated in the medical device 10 to generate a first magnetic field of a specific frequency due to resonance, and a drive coil 62 arranged around the position detection area to provide a magnetic field for position detection, which resonates the LC resonance circuit 61. The LC resonance circuit 61 includes an emission coil and a parasitic capacity or an additional capacity, and a resonance angle frequency is set to ω[rad]. The drive coil 62 provides an alternating magnetic field including a resonance frequency component with respect to the position detection area. In FIG. 13, only one drive coil 62 is shown, however, a plurality of the drive coils 62 can be arranged appropriately. The position detecting device 50 includes a drive unit 63 that drives the drive coil 62.

In the case of the medical device guiding system 1B according to the eighth embodiment, a method for creating the LUT 52 to be required can be the same as in the case of the medical device guiding system 1A, if it is considered that the medical device 10 is a source for generating the first magnetic field for position detection toward the position detection area. In the case of the eighth embodiment, because the drive coil 62 is arranged around the position detection area in addition to the guiding coil 21 and the drive coil 62 is also connected to the drive unit 63 having a low output impedance as in the guiding coil 21, the drive coil 62 is also a source of the unnecessary second magnetic field as viewed from the magnetic field detector 40. Accordingly, in the eighth embodiment, at the time of creating the LUT 52, the drive coil 62 is also a target to calculate the second magnetic field as in the guiding coil 21, and is included in one of the coils arranged around the position detection area to calculate the second magnetic field.

In the eighth embodiment, although not shown, a plurality of LUTs different for each connection mode with respect to the drive unit 24 of the guiding coil 21 and each connection mode with respect to the drive unit 63 of the drive coil 62 are prepared as the LUT 52, and the LUT 52 referred to by the magnetic field calculator 54 can be switched based on the information of the connection mode of the guiding coil 21 and the drive coil 62 acquired from the information acquiring unit 25 or a second information acquiring unit (not shown).

Ninth Embodiment

Figure 14:
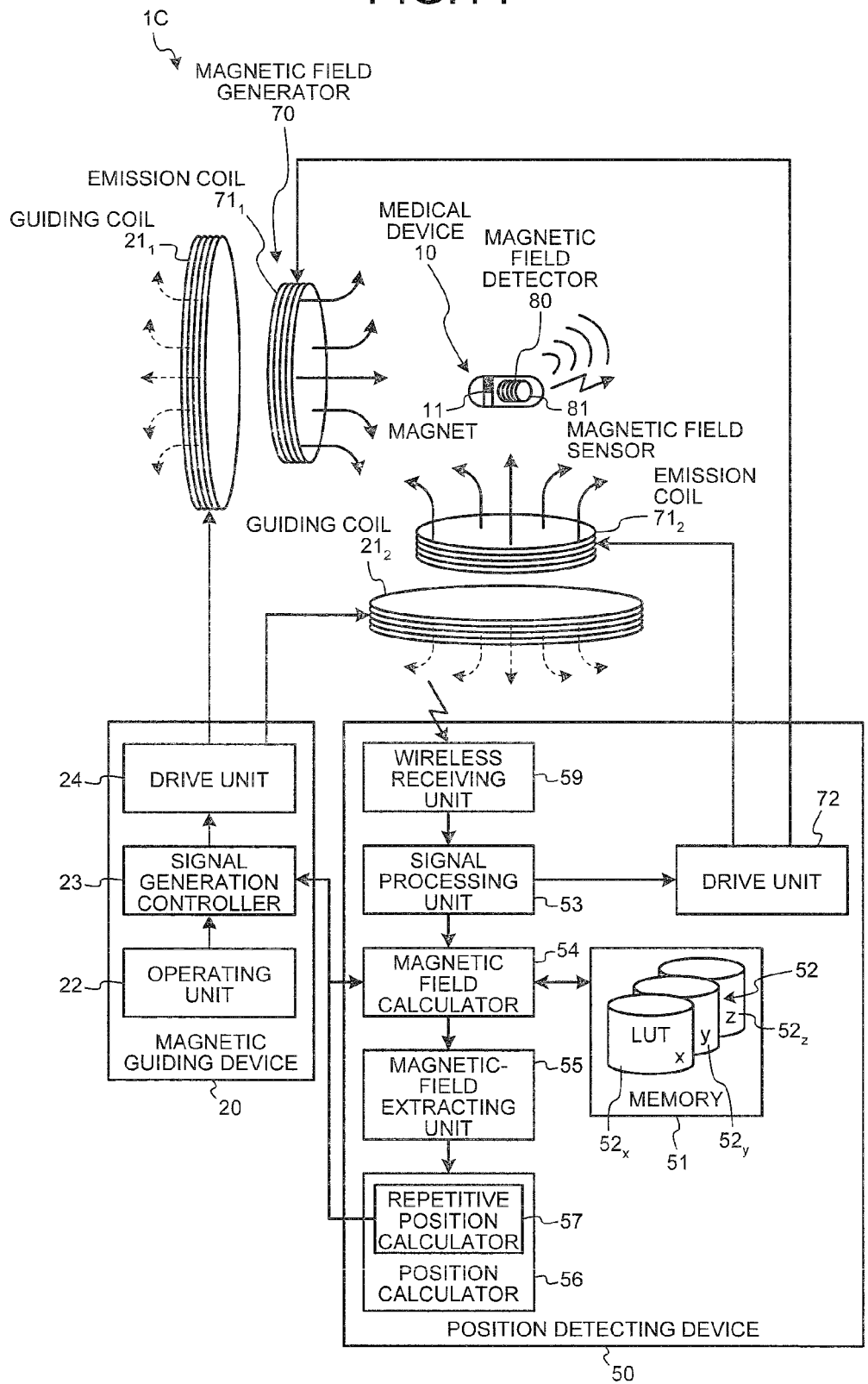
FIG. 14 is a schematic diagram of a fundamental configuration example of a medical device guiding system according to a ninth embodiment.

A ninth embodiment of the present invention is explained with reference to FIG. 14. FIG. 14 is a schematic diagram of a fundamental configuration example of a medical device guiding system according to the ninth embodiment of the present invention. In a medical device guiding system 10 according to the ninth embodiment, the position detecting device 50 includes a magnetic field generator 70 and a magnetic field detector 80 in which the arrangement of the magnetic field generator 30 and the magnetic field detector magnetic field detector is reversed. That is, it is a system that detects the position of the medical device 10 by providing a first magnetic field of a specific frequency for position detection from outside with respect to the position detection area, thereby capturing the first magnetic field for position detection by the magnetic field sensor incorporated in the medical device 10.

The magnetic field generator 70 includes a plurality of emission coils $71_1$ and $71_2$ arranged at known positions around the position detection area, to generate an alternating magnetic field of a specific frequency toward the position detection area. The position detecting device 50 includes a drive unit 72 that drives these emission coils $71_1$ and $71_2$.

The magnetic field detector 80 includes a magnetic field sensor 81 incorporated in the medical device 10 to detect a first magnetic field of a specific frequency generated by the emission coils $71_1$ and $71_2$, a signal processing unit (not shown) that converts magnetic field information detected by the magnetic field sensor 81 into a voltage signal, digitizes the voltage signal to generate transmission data and transmits the digitized signal to the outside of the medical device 10, and a wireless transmitting unit (not shown) that wirelessly transmits the signal-processed transmission data (magnetic field information detected by the magnetic field sensor 81) to the outside. Because the medical device 10 originally has a wireless function of wirelessly transmitting image information captured by an imaging device to the receiving device 15 (antenna 16) outside of the subject, the magnetic field information detected by the magnetic field sensor 81 can be added to or superimposed on the image information and wirelessly transmitted. The medical device 10 can include a separate wireless transmitting unit exclusive for the magnetic field information. The position detecting device 50 includes a wireless receiving unit 59 that wirelessly receives the magnetic field information transmitted from the wireless transmitting unit of the medical device 10. The wireless receiving unit 59 can use the external receiving device 15.

In the case of the configuration of the magnetic field generator 70 and the magnetic field detector 80 as described in the ninth embodiment, basically, the position and orientation of the medical device 10 are estimated to calculate the magnetic field strength and optimization calculation is performed so that a difference from the measurement value becomes minimum, thereby enabling to detect the position of the medical device 10.

However, when the guiding coils $21_1$ and $21_2$ are arranged around the position detection area, the second magnetic field that causes a change in a desired magnetic field distribution is guided and generated by mutual inductance with the emission coils $71_1$ and $71_2$ arranged around the position detection area.

Because the second magnetic field in this case is also determined only by the arrangement and shape of these coils $21_1$, $21_2$, $71_1$, and $71_2$, the second magnetic field can be calculated by calculation; however, the calculation becomes complicated and needs a very long time for consecutively calculating an unnecessary magnetic field at the time of position detection. In the ninth embodiment, therefore, as in the embodiments described above, when the medical device 10 is positioned at a preset specific position in a preset specific orientation in the position detection area, the LUT 52 in which the numerical information having a correlation with the second magnetic field generated at the position of the magnetic field sensor 81 in the medical device 10 by these coils $21_1$, $21_2$, $71_1$, and $71_2$ is stored, designating a plurality of specific positions and a plurality of specific orientations of the medical device 10 as variables are held in the memory 51 beforehand and referred to at the time of position detection. The second magnetic field is calculated by using the LUT 52 and is subtracted from the actual measurement value to calculate the corrected magnetic-field information, and optimization calculation is performed by using the corrected magnetic-field information, thereby performing position detection in a short time.

The LUT 52 according to the ninth embodiment requires two functions described below. A first function is a current flowing in the coils $21_1$, $21_2$, $71_1$, and $71_2$ due to the first magnetic field for position detection generated by the emission coils $71_1$ and $71_2$. When the emission coils $71_1$ and $71_2$ are divided into fine current elements and respectively designated as a magnetic-field generation source, the same calculation as in the case of calculating the influence to the guiding coil 21 explained in the first embodiment can be used.

A second function is a magnetic field generated at the position of the magnetic field sensor 81 of the medical device 10 by the coils $21_1$, $21_2$, $71_1$, and $71_2$ when the current flows. That is, a point to execute the calculation is at a point where the medical device 10 exists. The calculation is the same as a process for calculating the magnetic field generated at the position of the magnetic field sensor 41 by the respective guiding coils 21 according to the first embodiment; however, it is different from the first embodiment in that a point for calculating the magnetic field is not fixed by the medical device guiding system IC and it covers all the position detection area.

As an input, a position coordinate (x, y, z) is input, and a magnetic field strength for three axes of X-axis, Y-axis, and Z-axis can be obtained with respect to one point. As an operation of the position detecting device 50, the magnetic field at the respective estimated positions and estimated orientations in the middle of optimization calculation can be obtained, and data of three axes can be synthesized according to the estimated orientation of the medical device 10 to obtain the actual magnetic field.

In the method of the ninth embodiment, the mutual inductance with the respective coils $21_1$, $21_2$, $71_1$, and $71_2$ with respect to the position and orientation of the magnetic field sensor 81 can be calculated to create the LUT 52.

In the ninth embodiment, although not shown, a plurality of LUTs different for each connection mode with respect to the drive unit 24 of the guiding coil 21 and the connection mode with respect to the drive unit 72 of the emission coil 71 can be prepared, and the LUT 52 referred to by the magnetic field calculator 54 can be switched based on the information of the connection state of the guiding coil 21 and the emission coil 71 acquired from the information acquiring unit 25 or a third information acquiring unit (not shown).

In the medical device guiding system, the medical device guiding method, and the method for creating a look-up table to be used in the medical device guiding system according to the present invention, the second magnetic field, which is induced and generated at the position of the magnetic field detector by the guiding coil or the magnetic field generator due to the action of the first magnetic field, is calculated at the time of position detection, and the second magnetic field is subtracted from the first magnetic field detected by the magnetic field detector to calculate the corrected magnetic-field information. Therefore, accurate position detection becomes possible without being affected by the unnecessary second magnetic field. Further, because the second magnetic field is calculated by using a look-up table in which numerical information having a correlation with the second magnetic field induced and generated at the position of the magnetic field detector is stored beforehand, an amount of calculation performed each time can be reduced to enable high speed processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device guiding system comprising:
    a medical device having a built-in magnet and introduced into a body cavity;
    a position detecting device having a magnetic field generator and a magnetic field detector, one of the magnetic field generator and the magnetic field detector being incorporated in the medical device, wherein the magnetic field generator generates a first magnetic field of a specific frequency and the magnetic field detector detects magnetic-field information including the first magnetic field of the specific frequency, to detect at least one of a position and an orientation of the medical device; and
    a magnetic guiding device having a guiding coil that generates a guiding magnetic field for changing at least one of the position and the orientation of the medical device by acting on the magnet, and a drive unit connected to the guiding coil to supply power for generating the guiding magnetic field, wherein
    the position detecting device is arranged at a specific position detection area for estimating at least one of the position and the orientation of the medical device, and the position detecting device comprises:
    a look-up table that stores a plurality of pieces of numerical information having a correlation with a second magnetic field induced at a position of the magnetic field detector by at least one of the guiding coil and the magnetic field generator due to the action of the first magnetic field, when the medical device is arranged at a plurality of specific positions in a plurality of specific orientations;
    a magnetic field calculator that estimates, based on the position and the orientation of the medical device, the second magnetic field by referring to the look-up table;
    a magnetic-field extracting unit that calculates corrected magnetic-field information obtained by subtracting the second magnetic field estimated by the magnetic field calculator from the first magnetic field detected by the magnetic field detector; and
    a position calculator that estimates, based on the corrected magnetic-field information calculated by the magnetic field extracting unit, the position and the orientation of the medical device.

2. The medical device guiding system according to claim 1, wherein
    in the position detecting device, the magnetic field calculator estimates, based on at least one of the position and the orientation of the medical device estimated by the position calculator, the second magnetic field again by referring to the look-up table, the magnetic-field extracting unit calculates again the corrected magnetic-field information obtained by subtracting the second magnetic field estimated again from the magnetic-field information detected by the magnetic field detector, and the position calculator has a repetitive calculator that repetitively performs, based on the corrected magnetic-field information, calculation for estimating the position and the orientation of the medical device, and
    the repetitive calculator repetitively performs calculation until an amount of change in the again-estimated second magnetic field or the again-calculated corrected magnetic-field information becomes smaller than a set threshold.

3. The medical device guiding system according to claim 1, wherein
    the position detecting device obtains an estimated detection value obtained by estimating, based on the position and the orientation of the medical device estimated by the position calculator, a detection value of the magnetic field detector, the detection value being due to the first magnetic field,
    the magnetic field calculator estimates again, based on the position and the orientation of the medical device estimated by the position calculator, the second magnetic field by referring to the look-up table, the magnetic-field extracting unit calculates the corrected magnetic-field information obtained by subtracting the second magnetic field estimated again from the magnetic-field information detected by the magnetic field detector, and the position calculator has a repetitive calculator that repetitively performs, based on the corrected magnetic-field information, calculation for estimating the position and the orientation of the medical device, and
    the repetitive calculator repetitively performs calculation until the estimated detection value of the magnetic field detector and the corrected magnetic-field information substantially match each other.

4. The medical device guiding system according to claim 1, wherein
    the magnetic field generator includes an oscillation circuit and an emission coil incorporated in the medical device and generates the first magnetic field of the specific frequency,
    the magnetic field detector includes a plurality of magnetic field sensors arranged the position detection area, and
    the guiding coil induces the second magnetic field.

5. The medical device guiding system according to claim 1, wherein
    the magnetic field generator includes a drive coil arranged the position detection area and a resonance circuit including a capacitor and an emission coil incorporated in the medical device, and the resonance circuit resonates due to a magnetic field for position detection generated by the drive coil to generate the first magnetic field of a specific frequency outside thereof,
    the magnetic field detector includes a plurality of magnetic field sensors arranged the position detection area, and
    the guiding coil induces the second magnetic field.

6. The medical device guiding system according to claim 5, wherein the drive coil also induces the second magnetic field.

7. The medical device guiding system according to claim 1, wherein
the magnetic field generator includes a plurality of emission coils arranged the position detection area and generates the first magnetic field of a specific frequency,
the magnetic field detector is incorporated in the medical device,
the position detecting device includes a wireless transmitting unit incorporated in the medical device to wirelessly transmit the magnetic field information detected by the magnetic field detector to the outside of the medical device, and a wireless receiving unit provided outside of the medical device to receive the magnetic field information transmitted by the wireless transmitting unit, and
the guiding coil induces the second magnetic field.

8. The medical device guiding system according to claim 7, wherein the emission coil also induces the second magnetic field.

9. The medical device guiding system according to claim 1, wherein
the look-up table stores the numerical information for each of the specific positions discretely set in the position detection area, and
when the position of the medical device is between the specific positions, the magnetic field calculator refers to the look-up table at at least two specific positions putting the position of the medical device therebetween to calculate the second magnetic field according to interpolation calculation between the at least two specific positions.

10. The medical device guiding system according to claim 1, wherein the look-up table is individually provided for each axis of three linearly independent axes.

11. The medical device guiding system according to claim 10, wherein the linearly independent three axes are orthogonal to each other.

12. The medical device guiding system according to claim 1, wherein the look-up table stores numerical information having a correlation with the second magnetic field induced at the position of the magnetic field detector by the guiding coils or the magnetic field generator due to multiple interference of up to a preset order.

13. The medical device guiding system according to claim 1, wherein the look-up table calculates and stores numerical information having a correlation with the second magnetic field induced at the position of the magnetic field detector by the guiding coils or the magnetic field generator due to multiple interference, based on mutual inductance between the guiding coils or between the magnetic field detectors.

14. The medical device guiding system according to claim 1, wherein the look-up table stores numerical information having a correlation with the second magnetic field induced at the position of the magnetic field detector as information based on actual measurement data of an electric current flowing in the guiding coil or the magnetic field detector.

15. The medical device guiding system according to claim 1, further comprising a first information acquiring unit that acquires information regarding a connection mode of the guiding coil with respect to the drive unit, wherein
the position detecting device includes a plurality of look-up tables different for each connection mode of the guiding coil with respect to the drive unit, and the look-up table to be referred to by the magnetic field calculator is switched based on the information regarding the connection mode of the guiding coil.

16. The medical device guiding system according to claim 6, further comprising a first information acquiring unit that acquires information regarding a connection mode of the guiding coil with respect to the drive unit and a second information acquiring unit that acquires information regarding a connection mode of the drive coil, wherein
the position detecting device includes a plurality of look-up tables different for each connection mode of the guiding coil with respect to the drive unit and each connection mode of the drive coil, and the look-up table to be referred to by the magnetic field calculator is switched based on the information regarding the connection modes of the guiding coil and the drive coil.

17. The medical device guiding system according to claim 8, further comprising a first information acquiring unit that acquires information regarding a connection mode of the guiding coil with respect to the drive unit and a third information acquiring unit that acquires information regarding a connection mode of the emission coil, wherein
the position detecting device includes a plurality of look-up tables different for each connection mode of the guiding coil with respect to the emission unit and each connection mode of the emission coil, and the look-up table to be referred to by the magnetic field calculator is switched based on the information regarding the connection modes of the guiding coil and the emission coil.

18. The medical device guiding system according to claim 1, further comprising a fourth information acquiring unit that acquires impedance information of the guiding coil, wherein
the position detecting device includes a plurality of look-up tables different for each different specific impedance of the guiding coil, and the look-up table to be referred to by the magnetic field calculator is switched based on the impedance information of the guiding coil.

19. The medical device guiding system according to claim 18, wherein when the acquired impedance information of the guiding coil indicates an intermediate level of the specific impedances, the position detecting device refers to the look-up tables with two specific impedances putting the impedance information therebetween, to calculate the second magnetic field according to interpolation calculation between the two specific impedances.

20. The medical device guiding system according to claim 1, wherein
the look-up table is configured by being divided into:
a first look-up table in which numerical information having a correlation with an electric current flowing in the guiding coil due to guidance by the magnetic field generator is stored, designating position information of the magnetic field generator as a variable; and
a second look-up table in which numerical information having a correlation with the second magnetic field induced at the position of the magnetic field detector when a preset specific current is caused to flow in the guiding coil is stored, designating the position information of the magnetic field detector as a variable, and
the magnetic field calculator calculates the current flowing in the guiding coil by using impedance information of the guiding coil and the numerical information that is acquired by referring, based on the position information of the magnetic field generator, to the first look-up table, and calculates, based on the current calculated, the second magnetic field by referring to the second look-up table.

21. The medical device guiding system according to claim 1, wherein the look-up table is created based on a single filament model in which a coil included in the guiding coil or the magnetic field generator is approximated as one line.

22. The medical device guiding system according to claim 1, wherein the look-up table is created based on a multi-filament model in which a coil included in the guiding coil or the magnetic field generator is approximated as a plurality of lines.

23. The medical device guiding system according to claim 1, wherein the look-up table is created based on a coil model having a physical shape in which a coil included in the guiding coil or the magnetic field generator is created according to a finite element method.

24. A medical device guiding method for guiding and controlling a position or an orientation of a medical device having a built-in magnet and introduced into a body cavity, based on a result of detecting the position and the orientation of the medical device from a first magnetic field of a specific frequency, by using a position detecting device having a magnetic field generator and a magnetic field detector, one of the magnetic field generator and the magnetic field detector being incorporated in the medical device, the method comprising:

generating a guiding magnetic field acting on the magnet by a guiding coil supplied with power from a drive unit to control the position or the orientation of the medical device;

generating a first magnetic field of a specific frequency by the magnetic field generator;

detecting a magnetic field including the first magnetic field generated at the magnetic-field generating step by the magnetic field detector;

estimating, when the medical device is arranged at a plurality of specific positions in a plurality of specific orientations, a second magnetic field that is induced at a position of the magnetic field detector, by at least one of the guiding coil and the magnetic field generator, due to the action of the first magnetic field, wherein the estimating is carried out by referring, based on the position and the orientation of the medical device, to a look-up table, the look-up table storing a plurality of pieces of numerical information having a correlation with the second magnetic field;

calculating corrected magnetic-field information obtained by subtracting the estimated second magnetic field from the detected magnetic field; and estimating the position and the orientation of the medical device based on the calculated corrected magnetic-field information.

25. The medical device guiding method according to claim 24, wherein the estimating the position and orientation includes repetitively performing:

the estimating, based on the estimated position and orientation of the medical device, the second magnetic field by referring to the look-up; and the estimating the position and orientation of the medical device based on the calculated corrected magnetic-field information.

26. The medical device guiding method according to claim 24, wherein the estimating the position and orientation includes calculating estimated detected-magnetic-field information detected by the magnetic field detector based on the estimated position and orientation of the medical device; and repetitively performing the detecting and the calculating the estimated detected-magnetic-field-information until the corrected magnetic-field information substantially matches the estimated magnetic field.

27. The medical device guiding method according to claim 24, wherein the generating the first magnetic field includes generating the first magnetic field of a specific frequency by the magnetic field generator including an oscillation circuit and an emission coil incorporated in the medical device, and the detecting includes detecting the first magnetic field by the magnetic field detector including a plurality of magnetic field sensors arranged around a position detection area at which the position detecting device is arranged for estimating the position and the orientation of the medical device.

28. The medical device guiding method according to claim 24, wherein the generating the first magnetic field includes generating, in the magnetic field generator including a drive coil arranged around a position detection area at which the position detecting device is arranged for estimating the position and the orientation of the medical device to generate a magnetic field for position detection, and a resonance circuit including a capacitor and an emission coil incorporated in the medical device, the first magnetic field of a specific frequency outside thereof because of resonance of the resonance circuit due to the magnetic field for position detection, and the detecting includes detecting the first magnetic field by the magnetic field detector including a plurality of magnetic field sensors arranged the specific position detection area.

29. The medical device guiding method according to claim 24, wherein the generating the first magnetic field includes generating the first magnetic field of a specific frequency by the magnetic field generator including a plurality of emission coils arranged a position detection area at which the position detecting device is arranged for estimating the position and the orientation of the medical device, and the detecting includes detecting the first magnetic field by the magnetic field detector incorporated in the medical device.

30. The medical device guiding method according to claim 24, wherein a plurality of look-up tables different for each connection mode of the guiding coil with respect to the drive unit are used as the look-up table, and the method further comprises acquiring information of the connection mode of the guiding coil with respect to the drive unit to switch, based on the information of the connection mode, the look-up table to be referred to.

31. The medical device guiding method according to claim 28, wherein a plurality of look-up tables different for each connection mode of the guiding coil with respect to the drive unit and for each connection mode of the drive coil are used as the look-up table, and the method further comprises acquiring information of the connection mode of the guiding coil with respect to the drive unit and information of the connection mode of the drive coil to switch, based on pieces of information of the connection mode, the look-up table to be referred to.

32. The medical device guiding method according to claim 29, wherein a plurality of look-up tables different for each connection mode of the guiding coil with respect to the drive unit and for each connection mode of the emission coil are used as the look-up table, and the method further comprises acquiring information of the connection mode of the guiding coil with respect to the drive unit and information of the connection mode of the drive coil to switch, based on pieces of information of the connection modes, the look-up table to be referred to.

33. The medical device guiding method according to claim 24, wherein
a plurality of look-up tables different for each different specific impedance of the guiding coil are used as the look-up table, and
the method further comprises a table switching step of acquiring impedance information of the guiding coil to switch, based on the impedance information, the look-up table to be referred to.

34. The medical device guiding method according to claim 33, wherein
the estimating the second magnetic field includes, when the impedance information of the guiding coil indicates an intermediate level of the specific impedances, calculating the second magnetic field according to interpolation calculation between two specific impedances by referring to the look-up tables with the two specific impedances putting the impedance information therebetween.

35. The medical device guiding method according to claim 24, wherein
used as the look-up table are:
a first look-up table in which numerical information having a correlation with an electric current flowing in the guiding coil due to guidance by the magnetic field generator is stored, designating position information of the magnetic field generator as a variable; and
a second look-up table in which numerical information having a correlation with the second magnetic field induced at the position of the magnetic field detector when a preset specific current is caused to flow in the guiding coil is stored, designating the position information of the magnetic field detector as a variable, and
the estimating the first magnetic field includes calculating a current flowing in the guiding coil by using impedance information and the numerical information that is acquired by referring, based on the position information of the magnetic field generator, to the first look-up table, and calculating the second magnetic field by referring, based on the current calculated, to the second look-up table.

36. A method for creating a look-up table to be used in a medical device guiding system, the system comprising: a medical device having a built-in magnet and introduced into a body cavity; a position detecting device incorporated in the medical device and having a magnetic field generator including an emission coil and an oscillation circuit to generate a first magnetic field of a specific frequency, and a magnetic field detector including a plurality of magnetic field sensors arranged at a position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field, the method comprising:
setting a plurality of discrete specific positions and a plurality of discrete specific orientations within the position detection area;
calculating a magnetic flux penetrating a plurality of guiding coils arranged at known positions around the position detection area when the medical device is arranged at one specific position and in one specific orientation to generate the first magnetic field;
calculating an induction current flowing in the guiding coils based on calculated magnetic flux;
calculating numerical information having a correlation with a second magnetic field induced at the magnetic field sensors, when the calculated induction current flows in the guiding coils;
storing the calculated numerical information having the correlation with the second magnetic field in association with the one specific position and the one specific orientation; and
creating a table by repeating the calculating the magnetic flux, the calculating the induction current, the calculating the numerical information, and the storing for all the specific positions and the specific orientations, by sequentially changing the one specific position and the one specific orientation.

37. The method for creating a look-up table to be used in a medical device guiding system according to claim 36, wherein at the calculating the magnetic flux, the calculated magnetic flux includes a magnetic flux generated by multiple interference of up to a preset order between the guiding coils arranged the position detection area.

38. A method for creating a look-up table to be used in a medical device guiding system, the system comprising: a medical device having a built-in magnet and introduced into a body cavity; a position detecting device incorporated in the medical device and having a magnetic field generator including an emission coil and an oscillation circuit to generate a first magnetic field of a specific frequency and a magnetic field detector including a plurality of magnetic field sensors arranged at a position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field, the method comprising:
setting a plurality of discrete specific positions and a plurality of discrete specific orientations within the position detection area;
calculating mutual inductance with a plurality of guiding coils arranged at known positions around the position detection area when the medical device is arranged at one specific position and in one specific orientation to generate the first magnetic field;
calculating an induction current flowing in the respective guiding coils based on calculated mutual inductance;
calculating numerical information having a correlation with a second magnetic field induced at the magnetic field sensors arranged the position detection area to detect the first magnetic field, when the calculated induction current flows in the guiding coils;
storing the calculated numerical information having the correlation with the second magnetic field in association with the one specific position and the one specific orientation; and
creating a table by repeating the calculating the induction current, the calculating the numerical information, and the storing for all the specific positions and specific orientations, by sequentially changing the one specific position and the one specific orientation.

39. A method for creating a look-up table to be used in a medical device guiding system, the system comprising: a medical device having a built-in magnet and introduced into a body cavity; a position detecting device that includes a magnetic field generator including a drive coil arranged at a position detection area to generate a magnetic field for position detection and a resonance circuit including an emission coil and a capacitor, incorporated in the medical device to resonate due to the magnetic field for position detection, thereby generating a first magnetic field of a specific frequency, and a magnetic field detector including a plurality of magnetic field sensors arranged at the position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field, the method comprising:

setting a plurality of discrete specific positions and a plurality of discrete specific orientations within the position detection area;

calculating a magnetic flux penetrating a plurality of guiding coils arranged at known positions around the position detection area or the drive coil, when the medical device is arranged at one specific position and in one specific orientation to generate the first magnetic field;

calculating an induction current flowing in the guiding coils or the drive coil based on the calculated magnetic flux;

calculating numerical information having a correlation with a second magnetic field induced at positions of the magnetic field sensors, when the calculated induction current flows in the guiding coils or the drive coil;

storing the calculated numerical information having the correlation with the second magnetic field in association with the one specific position and the one specific orientation; and creating a table by repeating the calculating the magnetic flux, the calculating the induction current, the calculating the numerical information, and the storing for all the specific positions and the specific orientations, by sequentially changing the one specific position and the one specific orientation.

40. The method for creating a look-up table to be used in a medical device guiding system according to claim 39, wherein at the calculating the magnetic flux, the calculated magnetic flux includes a magnetic flux generated by multiple interference of up to a preset order between the guiding coils arranged the position detection area or between the drive coils.

41. A method for creating a look-up table to be used in a medical device guiding system, the system comprising: a medical device having a built-in magnet and introduced into a body cavity; a position detecting device that includes a magnetic field generator including a drive coil arranged at a position detection area to generate a magnetic field for position detection and a resonance circuit including an emission coil and a capacitor, incorporated in the medical device to resonate due to the magnetic field for position detection, thereby generating a first magnetic field of a specific frequency, and a magnetic field detector including a plurality of magnetic field sensors arranged at the position detection area to detect a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field, the method comprising:

setting a plurality of discrete specific positions and a plurality of discrete specific orientations within the position detection area;

calculating mutual inductance with a plurality of guiding coils arranged at known positions around the position detection area or the drive coil, when the medical device is arranged at one specific position and in one specific orientation to generate the first magnetic field;

calculating an induction current flowing in the respective guiding coils or the drive coil based on the calculated mutual inductance;

calculating numerical information having a correlation with a second magnetic field induced at positions of the magnetic field sensors arranged the position detection area to detect the first magnetic field, when the calculated induction current flows in the guiding coils or the drive coil;

storing the calculated numerical information having the correlation with the second magnetic field in association with the one specific position and the one specific orientation; and creating a table by repeating the calculating the induction current, the calculating the numerical information, and the storing for all the specific positions and the specific orientations, by sequentially changing the one specific position and the one specific orientation.

42. A method for creating a look-up table to be used in a medical device guiding system, the system comprising: a medical device having a built-in magnet and introduced into a body cavity; a position detecting device having a magnetic field generator including a plurality of emission coils arranged at a position detection area to generate a first magnetic field of a specific frequency and a magnetic field detector including a magnetic field sensor incorporated in the medical device to detect the first magnetic field, thereby detecting a position and an orientation of the medical device based on the first magnetic field; and a magnetic guiding device having a guiding coil that generates a guiding magnetic field for changing the position or the orientation of the medical device by acting on the magnet and a drive unit connected to the guiding coil to supply power for generating the guiding magnetic field, the method comprising:

setting a plurality of discrete specific positions and a plurality of discrete specific orientations within the position detection area;

calculating an induction current flowing in the guiding coil or the emission coil arranged at a known position around the position detection area, when the medical device is arranged at one specific position and in one specific orientation to generate the first magnetic field of a specific frequency with respect to the position detection area by the emission coil;

calculating numerical information having a correlation with a second magnetic field induced at a position of the magnetic field sensor, when the calculated induction current flows in the guiding coil or the emission coil;

storing the calculated numerical information having the correlation with the second magnetic field in association with the one specific position and the one specific orientation; and creating a table by repeating the calculating the induction current, the calculating the numerical information, and the storing for all the specific positions and specific orientations, by sequentially changing the one specific position and the one specific orientation.

43. The method for creating a look-up table to be used in a medical device guiding system according to claim 38, wherein the look-up table is created based on a single filament model in which the guiding coil is approximated as one line.

44. The method for creating a look-up table to be used in a medical device guiding system according to claim 38, wherein the look-up table is created based on a multi-filament model in which the guiding coil is approximated as a plurality of lines.

45. The method for creating a look-up table to be used in a medical device guiding system according to claim 38, wherein the look-up table is created based on a coil model having a physical shape in which the guiding coil is created according to a finite element method.

46. The method for creating a look-up table to be used in a medical device guiding system according to claim 39, wherein the look-up table is created based on a single filament model in which the drive coil or guiding coil is approximated as one line.

47. The method for creating a look-up table to be used in a medical device guiding system according to claim 39, wherein the look-up table is created based on a multi-filament model in which the drive coil or guiding coil is approximated as a plurality of lines.

48. The method for creating a look-up table to be used in a medical device guiding system according to claim 39, wherein the look-up table is created based on a coil model having a physical shape in which the drive coil or guiding coil is created according to a finite element method.

49. The method for creating a look-up table to be used in a medical device guiding system according to claim 41, wherein the look-up table is created based on a single filament model in which the drive coil or guiding coil is approximated as one line.

50. The method for creating a look-up table to be used in a medical device guiding system according to claim 41, wherein the look-up table is created based on a multi-filament model in which the drive coil or guiding coil is approximated as a plurality of lines.

51. The method for creating a look-up table to be used in a medical device guiding system according to claim 41, wherein the look-up table is created based on a coil model having a physical shape in which the drive coil or guiding coil is created according to a finite element method.

52. The method for creating a look-up table to be used in a medical device guiding system according to claim 42, wherein the look-up table is created based on a single filament model in which the guiding coil or emission coil is approximated as one line.

53. The method for creating a look-up table to be used in a medical device guiding system according to claim 42, wherein the look-up table is created based on a multi-filament model in which the guiding coil or emission coil is approximated as a plurality of lines.

54. The method for creating a look-up table to be used in a medical device guiding system according to claim 42, wherein the look-up table is created based on a coil model having a physical shape in which the guiding coil or emission coil is created according to a finite element method.

55. The medical device guiding system according to claim 1, wherein the detected magnetic-field information and the corrected magnetic-field information are amplitude information of the magnetic field.

56. The medical device guiding system according to claim 1, wherein the detected magnetic-field information and the corrected magnetic-field information are amplitude information and phase information of the magnetic field.

57. The medical device guiding system according to claim 24, wherein detected magnetic-field information and the corrected magnetic-field information are amplitude information of the magnetic field.

58. The medical device guiding system according to claim 24, wherein detected magnetic-field information and the corrected magnetic-field information are amplitude information and phase information of the magnetic field.

* * * * *